United States Patent
Oka et al.

(10) Patent No.: US 11,692,216 B2
(45) Date of Patent: Jul. 4, 2023

(54) METHOD FOR ASSISTING PREDICTION OF RISK OF OCCURRENCE OF SIDE EFFECT OF IRINOTECAN

(71) Applicants: YAMAGUCHI UNIVERSITY, Yamaguchi (JP); TOYO KOHAN CO., LTD., Tokyo (JP)

(72) Inventors: Masaaki Oka, Yamaguchi (JP); Shoichi Hazama, Yamaguchi (JP); Ryouichi Tsunedomi, Yamaguchi (JP)

(73) Assignees: YAMAGUCHI UNIVERSITY, Yamaguchi (JP); TOYO KOHAN CO., LTD., Tokyo (JP)

( * ) Notice: Subject to any disclaimer, the term of this patent is extended or adjusted under 35 U.S.C. 154(b) by 0 days.

(21) Appl. No.: 16/788,406

(22) Filed: Feb. 12, 2020

(65) Prior Publication Data

US 2020/0172966 A1 Jun. 4, 2020

Related U.S. Application Data

(62) Division of application No. 15/549,823, filed as application No. PCT/JP2016/000793 on Feb. 16, 2016, now abandoned.

(30) Foreign Application Priority Data

Feb. 17, 2015 (JP) .................. 2015-028813

(51) Int. Cl.
*C12Q 1/6886* (2018.01)
*C12Q 1/6827* (2018.01)
(Continued)

(52) U.S. Cl.
CPC ............. *C12Q 1/6827* (2013.01); *C12Q 1/68* (2013.01); *C12Q 1/6809* (2013.01);
(Continued)

(58) Field of Classification Search
CPC ...... C12Q 1/68; C12Q 1/5827; C12Q 1/2876; C12Q 1/6886; C12Q 1/6809;
(Continued)

(56) References Cited

U.S. PATENT DOCUMENTS

2013/0324503 A1 12/2013 Payami et al.

FOREIGN PATENT DOCUMENTS

JP 2005-504759 A 2/2005
JP 2005-506971 A 3/2005
(Continued)

OTHER PUBLICATIONS

Rs9425343 Ref SNP Report-dbSNP—NCBI; https://www.ncbi.nlm.nih.gov/projects/SNP/snpss.cgi?subsnpd=ss12998007 downloaded Aug. 6, 2020.
(Continued)

*Primary Examiner* — Diana B Johannsen
(74) *Attorney, Agent, or Firm* — Edwin S. Flores; Daniel J. Chalker; Chalker Flores, LLP

(57) ABSTRACT

An object of the present invention is to provide a simple and efficient device for predicting a risk of occurrence of a side effect of irinotecan by analyzing a single nucleotide polymorphism in a region encoding a specific gene. The prediction of the risk of the occurrence of a side effect of irinotecan is assisted by analyzing a single nucleotide polymorphism in a region encoding the APCDD1L gene, the R3HCC1 gene, the OR5I2 gene, the MKKS gene, the EDEM3 gene, or the ACOX1 gene which are present on genomic DNA in a biological sample collected from a test subject; or a single nucleotide polymorphism which is in linkage disequilibrium with or genetically linked to the single nucleotide polymorphism, and determining whether the single nucleotide poly-
(Continued)

morphism is homozygous for a variant type, heterozygous, or homozygous for a wild-type.

8 Claims, 10 Drawing Sheets

Specification includes a Sequence Listing.

(51) Int. Cl.
- C12Q 1/68 (2018.01)
- C12Q 1/6809 (2018.01)
- C12Q 1/6876 (2018.01)
- G01N 33/50 (2006.01)

(52) U.S. Cl.
CPC ....... *C12Q 1/6876* (2013.01); *G01N 33/5014* (2013.01); *C12Q 2600/106* (2013.01); *C12Q 2600/118* (2013.01); *C12Q 2600/142* (2013.01); *C12Q 2600/156* (2013.01); *C12Q 2600/158* (2013.01)

(58) Field of Classification Search
CPC ........ C12Q 2600/106; C12Q 2600/156; C12Q 2600/118; C12Q 2600/142; C12Q 2600/158
See application file for complete search history.

(56) References Cited

FOREIGN PATENT DOCUMENTS

| | | |
|---|---|---|
| JP | 2005-508312 A | 3/2005 |
| JP | 2008-072913 A | 4/2008 |
| JP | 2010-000018 A | 1/2010 |
| JP | 2011-250726 A | 12/2011 |
| JP | 2012-200251 A | 10/2012 |
| WO | 2002048400 A1 | 6/2002 |

OTHER PUBLICATIONS

Cha P. C. et al., "Single nucleotide polymorphism in ABCG2 is associated with irinotecan-induced severe myelosuppression," Journal of Human Genetics, 2009, vol. 54, p. 572-580, Abstract, Table 3.

Di Martino M. T. et al., "Single nucleotide polymorphisms of ABCC5 and ABCG1 transporter genes correlate to Irinotecan-associated gastrointestinal toxicity in colorectal cancer patients," Cancer Biology & Therapy, 2011, vol. 12, No. 9, p. 780-787 Abstract, Table 2.

Han J. Y. et al., "A genome-wide association study for irinotecan-related severe toxicities in patients with advanced non-small-cell lung cancer," The Pharmacogenomics Journal, 2013 vol. 13, p. 417-422, Abstract, Introduction, Results, paragraph 1.

Hazama et al., "UGT1A1*6,1A7*3, and 1A9*22 genotypes predict severe neutropenia in FOLFIRI-treated metastatic colorectal cancer in two prospective studies in Japan" Cancer Science, 104:1662-9 (2013).

Hoskins J. M. et al., "Irinotecan Pharmacogenetics: Influence of Pharmacodynamic Genes," Clinical Cancer Research, 2008, vol. 14, No. 6, p. 1788-1796.

Kobayashi, Hatasu, "The latest neuroscience information: Genetic mutation in moyamoya disease," Clinical Neuroscience, 2013, vol. 31, No. 12, pp. 1456-1457, p. 1456, left column non-official translation.

Kumar, P et al., "Predicting the effects of coding non-synonymous variants on protein function using the SIFT algorithm," Nature Protocols, 2009, vol. 4, No. 7, pp. 1073-1081, entire text.

McKenna, A. et al., "The Genome Analysis Toolkit: a MapReduce framework for analyzing next-generation DNA sequencing data," Genome Research, 2010, vol. 20, pp. 1297-1303, entire text, esp. abstract.

Ramensky, V. et al., "Human non-synonymous SNPs: server and survey," Nucleic Acids Research, 2002, vol. 30, No. 17, pp. 3894-3900, entire text, esp. abstract.

Takahashi H. et al., "Application of a Combination of a Knowledge-Based Algorithm and 2-Stage Screening to Hypothesis-Free Genomic Data on Irinotecan-Treated Patients for Identification of a Candidate Single Nucleotide Polymorphism Related to an Adverse Effect," PLoS One, 2014, vol. 9, No. 8, e105160, Abstract, Figure 3.

Tsunedomi et al., "A novel system for predicting the toxicity of irinotecan based an statistical pattern recognition with UGT1A genotypes" International Journal of Oncology, 45(4):1381-1390 (2014).

International Preliminary Report on Patentability PCT/JP2016/000793 dated Aug. 17, 2017.

NCBI, disclosure of rs1980576 probe on Illumina HumanOmni1-Quad_v1-0_b (2006).

Dong, MA et al. "Association of UGT1A1 * 28 Polymorphism with Toxicity and Efficacy of Innotecan in Chinese Patients" Journal of Sun Yat-Sen University (Medical Sciences) vol. 32, No. Jul. 4, 2011, pp. 495.

FIGURE 2

GATA2

Group 1
No side effect: Control
(No UGT variant)
wild-homo:      0
hetero:         2
variant homo:   3

| Case 1 |
| Case 2 |
| Case 3 |
| Case 4 |
| Case 5 |

Group 2
Side effect observed
(No UGT variant)
wild-homo:      4
hetero:         1
variant homo:   0

| Case 6 |
| Case 7 |
| Case 8 |
| Case 9 |
| Case 10 |

Group 3
G4 side effect observed since
the initial time
(UGT variants were included)
wild-homo:      3
hetero:         2
variant homo:   0

| Case 11 |
| Case 12 |
| Case 13 |
| Case 14 |
| Case 15 |

Standardized
Difference
= 1.71 (Rank_9)

A164T
(Gcc/Acc)
rs2335052

FIGURE 5

METHOD FOR ASSISTING PREDICTION OF
RISK OF OCCURRENCE OF SIDE EFFECT
OF IRINOTECAN

CROSS-REFERENCE TO RELATED APPLICATIONS

This patent application is a divisional application of U.S. patent application Ser. No. 15/549,823 filed on Aug. 9, 2017 and which claims priority to International Application No. PCT/JP2016/000793, filed on Feb. 16, 2016 claiming the priority of JP 2015-028813, filed on Feb. 17, 2015, the content of each of which is incorporated by reference herein.

INCORPORATION-BY-REFERENCE OF MATERIALS FILED ON COMPACT DISC

The present application includes a Sequence Listing which has been submitted in ASCII format via EFS-Web and is hereby incorporated by reference in its entirety. Said ASCII copy, created on Jun. 29, 2017, is named HRTA1026DIV_SL.txt and is 15, kilobytes in size.

TECHNICAL FIELD OF THE INVENTION

The present invention relates to a method for assisting a prediction of a risk of occurrence of a side effect of irinotecan, and to a probe or primer for use in analyzing single nucleotide polymorphisms in the method.

Irinotecan (CPT-11: 1,4'-Bipiperidine-1'-carboxylic acid (S)-4,11-diethyl-3,4,12,14-tetrahydro-4-hydroxy-3,14-dioxo-1H-pyrano[3',4':6,7]indolizino[1,2-b]quinolin-9-yl ester (CAS NO: 97682-44-5)) is an anticancer agent which is synthesized from camptothecin, a *Camptotheca*-derived anti-tumor alkaloid, and has been known to be useful in treating cancer such as lung cancer and metastatic colon cancer. Irinotecan inhibits the activity of a topoisomerase, an enzyme that promotes DNA replication, thereby exhibiting a potent anti-cancer effect. However, several serious side effects have been reported, including leucopenia, neutropenia, and diarrhea.

Recently, personalized medicine (i.e., individualized medicine), in which an optimal treatment approach is designed for each patient, has been partly put into practice. Regarding irinotecan, methods for predicting a side effect of irinotecan have been disclosed (see Patent Documents 1 to 4 and Non-Patent Documents 1 and 2), including detecting polymorphisms (e.g., UGT1A1*28, UGT1A1*6, UGT1A1*27, UGT1A1*60) of the UGT1A1 gene, which is a gene encoding a UDP-glucuronosyltransferase (UGT). Such methods have been used to predict a side effect of irinotecan and are being utilized to provide an indicator for personalized medicine.

Meanwhile, a kit for determining the genetic status of UGT1A1*28 and UGT1A1*6 (manufactured by Sekisui Medical Inc) is commercially available so as to predict whether or not there is a side effect of irinotecan.

To date, however, irinotecan has a side effect in 43% of patients who have been identified as non-high-risk patients based on polymorphisms of the UGT1A gene, for example, patients who are homozygous for a variant type of either UGT1A1*28 or UGT1A1*6 or who are heterozygous for both. In view of the current situation, a novel method has been sought which assists the prediction of the risk of the occurrence of a side effect of irinotecan.

PRIOR ART DOCUMENTS

Patent Documents

Patent Document 1: WO2002-048400
Patent Document 2: Japanese Unexamined Patent Application Publication No. 2011-250726
Patent Document 3: Japanese Unexamined Patent Application Publication No. 2010-000018
Patent Document 4: Japanese Unexamined Patent Application Publication No. 2008-072913

Non-Patent Documents

Non-Patent Document 1: Hazama et al., Cancer Science, 104: 1662-9 (2013)
Non-Patent Document 2: Tsunedomi et al., International Journal of Oncology, 45(4): 1381-1390 (2014)

SUMMARY OF THE INVENTION

Object to be Solved by the Invention

What is called personalized medicine has been sought by enabling the prediction of the risk of the occurrence of a side effect of an anti-cancer agent irinotecan during cancer treatment of individual patients and by providing treatment using an anti-cancer agent fit for each cancer patient. Here, an object of the present invention is to provide a simple and efficient device for predicting the risk of the occurrence of a side effect of irinotecan by analyzing a single nucleotide polymorphism in a region encoding a specific gene.

Means to Solve the Object

Comprehensive genomic analysis (exome analysis) was performed on patients who had been grouped based on clinical information (the presence or absence of the occurrence of a side effect of irinotecan) and information on polymorphisms of the UGT1A gene. This made it possible to search for novel irinotecan-side-effect-related factors not involving the polymorphisms of the UGT1A gene. The results have demonstrated that a single nucleotide polymorphism in a region encoding the APCDD1L gene, the R3HCC1 gene, the OR51I2 gene, the MKKS gene, the EDEM3 gene, or the ACOX1 gene or a single nucleotide polymorphism which is in linkage disequilibrium with or genetically linked to the former single nucleotide polymorphism is a factor used to assist the prediction of the risk of the occurrence of a side effect of irinotecan; and such a single nucleotide polymorphism is not linked to (associated with) the polymorphisms of the UGT1A gene. In this way, the present invention has been completed.

Specifically, the present invention relates to the following.
(1) A method for assisting a prediction of a risk of occurrence of a side effect of irinotecan, comprising analyzing a single nucleotide polymorphism in a region encoding APCDD1L gene, R3HCC1 gene, OR51I2 gene, MKKS gene, EDEM3 gene, or ACOX1 gene which is present on genomic DNA in a biological sample collected from a test subject; or a single nucleotide polymorphism which is in linkage disequilibrium with or genetically linked to the former single nucleotide polymorphism, and determining whether the single nucleotide polymorphism is homozygous for a variant type, homozygous for a wild-type, or heterozygous.

(2) The method according to "1", wherein the single nucleotide polymorphism in a region encoding APCDD1L gene, R3HCC1 gene, OR51I2 gene, MKKS gene, EDEM3 gene, or ACOX1 gene is any one of the following (a) to (g):

(a) a single nucleotide polymorphism present at nucleotide 186 of the nucleotide sequence encoding the APCDD1L gene and set forth in SEQ ID NO: 1 or a complementary sequence thereof;

(b) a single nucleotide polymorphism present at nucleotide 358 of the nucleotide sequence encoding the R3HCC1 gene and set forth in SEQ ID NO: 2 or a complementary sequence thereof;

(c) a single nucleotide polymorphism present at nucleotide 400 of the nucleotide sequence encoding the OR51I2 gene and set forth in SEQ ID NO: 3 or a complementary sequence thereof;

(d) a single nucleotide polymorphism present at nucleotide 1549 of the nucleotide sequence encoding the MKKS gene and set forth in SEQ ID NO: 4 or a complementary sequence thereof;

(e) a single nucleotide polymorphism present at nucleotide 2459 of the nucleotide sequence encoding the EDEM3 gene and set forth in SEQ ID NO: 5 or a complementary sequence thereof;

(f) a single nucleotide polymorphism present at nucleotide 238 of the nucleotide sequence encoding the APCDD1L gene and set forth in SEQ ID NO: 1 or a complementary sequence thereof; and (g) a single nucleotide polymorphism present at nucleotide 936 of the nucleotide sequence encoding the ACOX1 gene and set forth in SEQ ID NO: 6 or a complementary sequence thereof.

(3) The method according to "2", comprising assisting to predict that the risk of occurrence of a side effect of irinotecan is high when the single nucleotide polymorphism is homozygous for a variant type with respect to the single nucleotide polymorphism set forth in (a), (b), or (d) or when the single nucleotide polymorphism is homozygous for a wild-type with respect to the single nucleotide polymorphism set forth in (c), (e), (f), or (g).

(4) The method according to any one of "1" to "3", wherein the side effect is leucopenia or neutropenia.

(5) A probe for use in analyzing a single nucleotide polymorphism in the method according to any one of "1" to "4", which is any one of the following (h) to (n):

(h) a probe consisting of an oligonucleotide that hybridizes, under a stringent condition, with a sequence of 5 to 50 consecutive nucleotides containing a single nucleotide polymorphism site present at nucleotide 186 of the nucleotide sequence encoding APCDD1L gene and set forth in SEQ ID NO: 1 or a complementary sequence thereof;

(i) a probe consisting of an oligonucleotide that hybridizes, under a stringent condition, with a sequence of 5 to 50 consecutive nucleotides containing a single nucleotide polymorphism site present at nucleotide 358 of the nucleotide sequence encoding R3HCC1 gene and set forth in SEQ ID NO: 2 or a complementary sequence thereof;

(j) a probe consisting of an oligonucleotide that hybridizes, under a stringent condition, with a sequence of 5 to 50 consecutive nucleotides containing a single nucleotide polymorphism site present at nucleotide 400 of the nucleotide sequence encoding OR51I2 gene and set forth in SEQ ID NO: 3 or a complementary sequence thereof;

(k) a probe consisting of an oligonucleotide that hybridizes, under a stringent condition, with a sequence of 5 to 50 consecutive nucleotides containing a single nucleotide polymorphism site present at nucleotide 1549 of the nucleotide sequence encoding MKKS gene and set forth in SEQ ID NO: 4 or a complementary sequence thereof;

(l) a probe consisting of an oligonucleotide that hybridizes, under a stringent condition, with a sequence of 5 to 50 consecutive nucleotides containing a single nucleotide polymorphism site present at nucleotide 2459 of the nucleotide sequence encoding EDEM3 gene and set forth in SEQ ID NO: 5 or a complementary sequence thereof;

(m) a probe consisting of an oligonucleotide that hybridizes, under a stringent condition, with a sequence of 5 to 50 consecutive nucleotides containing a single nucleotide polymorphism site present at nucleotide 238 of the nucleotide sequence encoding APCDD1L gene and set forth in SEQ ID NO: 1 or a complementary sequence thereof; and (n) a probe consisting of an oligonucleotide that hybridizes, under a stringent condition, with a sequence of 5 to 50 consecutive nucleotides containing a single nucleotide polymorphism site present at nucleotide 936 of the nucleotide sequence encoding ACOX1 gene and set forth in SEQ ID NO: 6 or a complementary sequence thereof.

(6) A primer for use in analyzing a single nucleotide polymorphism in the method according to any one of "1" to "4", which is any one of the following (o) to (u):

(o) a primer consisting of an oligonucleotide that can amplify at least 5 consecutive nucleotides containing a single nucleotide polymorphism site present at nucleotide 186 of the nucleotide sequence encoding APCDD1L gene and set forth in SEQ ID NO: 1;

(p) a primer consisting of an oligonucleotide that can amplify at least 5 consecutive nucleotides containing a single nucleotide polymorphism site present at nucleotide 358 of the nucleotide sequence encoding R3HCC1 gene and set forth in SEQ ID NO: 2;

(q) a primer consisting of an oligonucleotide that can amplify at least 5 consecutive nucleotides containing a single nucleotide polymorphism site present at nucleotide 400 of the nucleotide sequence encoding OR51I2 gene and set forth in SEQ ID NO: 3;

(r) a primer consisting of an oligonucleotide that can amplify at least 5 consecutive nucleotides containing a single nucleotide polymorphism site present at nucleotide 1549 of the nucleotide sequence encoding MKKS gene and set forth in SEQ ID NO: 4;

(s) a primer consisting of an oligonucleotide that can amplify at least 5 consecutive nucleotides containing a single nucleotide polymorphism site present at nucleotide 2459 of the nucleotide sequence encoding EDEM3 gene and set forth in SEQ ID NO: 5;

(t) a primer consisting of an oligonucleotide that can amplify at least 5 consecutive nucleotides containing a single nucleotide polymorphism site present at nucleotide 238 of the nucleotide sequence encoding APCDD1L gene and set forth in SEQ ID NO: 1; and (u) a primer consisting of an oligonucleotide that can amplify at least 5 consecutive nucleotides containing a single nucleotide polymorphism site present at nucleotide 936 of the nucleotide sequence encoding ACOX1 gene and set forth in SEQ ID NO: 6.

(7) A kit for assisting a prediction of a risk of occurrence of a side effect of irinotecan, comprising the probe according to "5" or the primer according to "6".

Effect of the Invention

The present invention makes it possible to assist a prediction of a risk of occurrence of a side effect of irinotecan. The prediction of the side effect in each patient by using such a method enables treatment, what is called personalized medicine, using an anti-cancer agent fit for each patient with cancer.

BRIEF DESCRIPTION OF DRAWINGS

Figure 2:
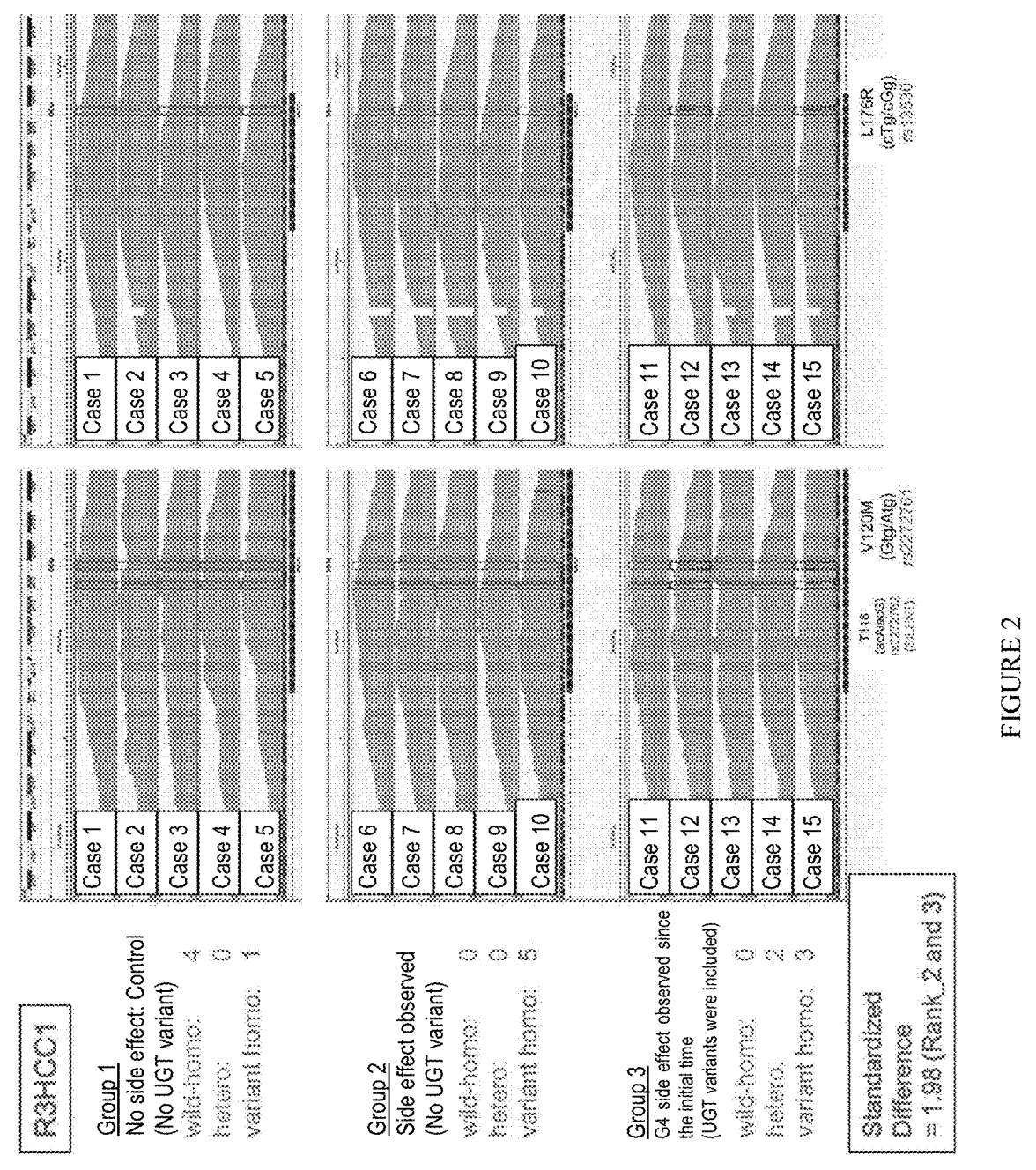

FIG. 2 is diagrams illustrating the results of subjecting the R3HCC1 gene-encoding region to exome analysis.

FIG. 5 is diagrams illustrating the results of subjecting the GATA2 gene-encoding region to exome analysis.

MODE OF CARRYING OUT THE INVENTION

Figure 1:
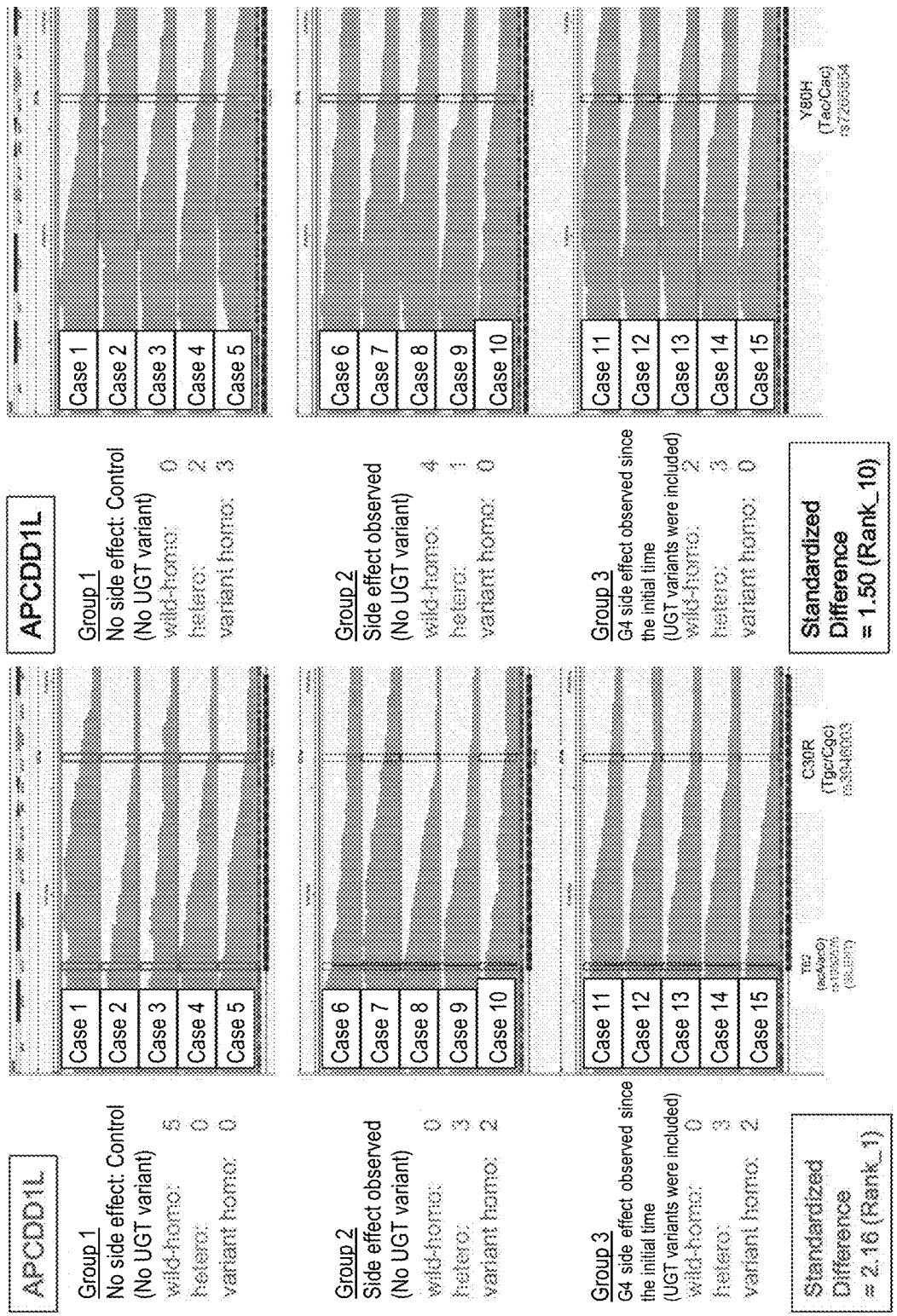
FIG. 1 is diagrams illustrating the results of subjecting the APCDD1L gene-encoding region to exome analysis.
Figure 3:
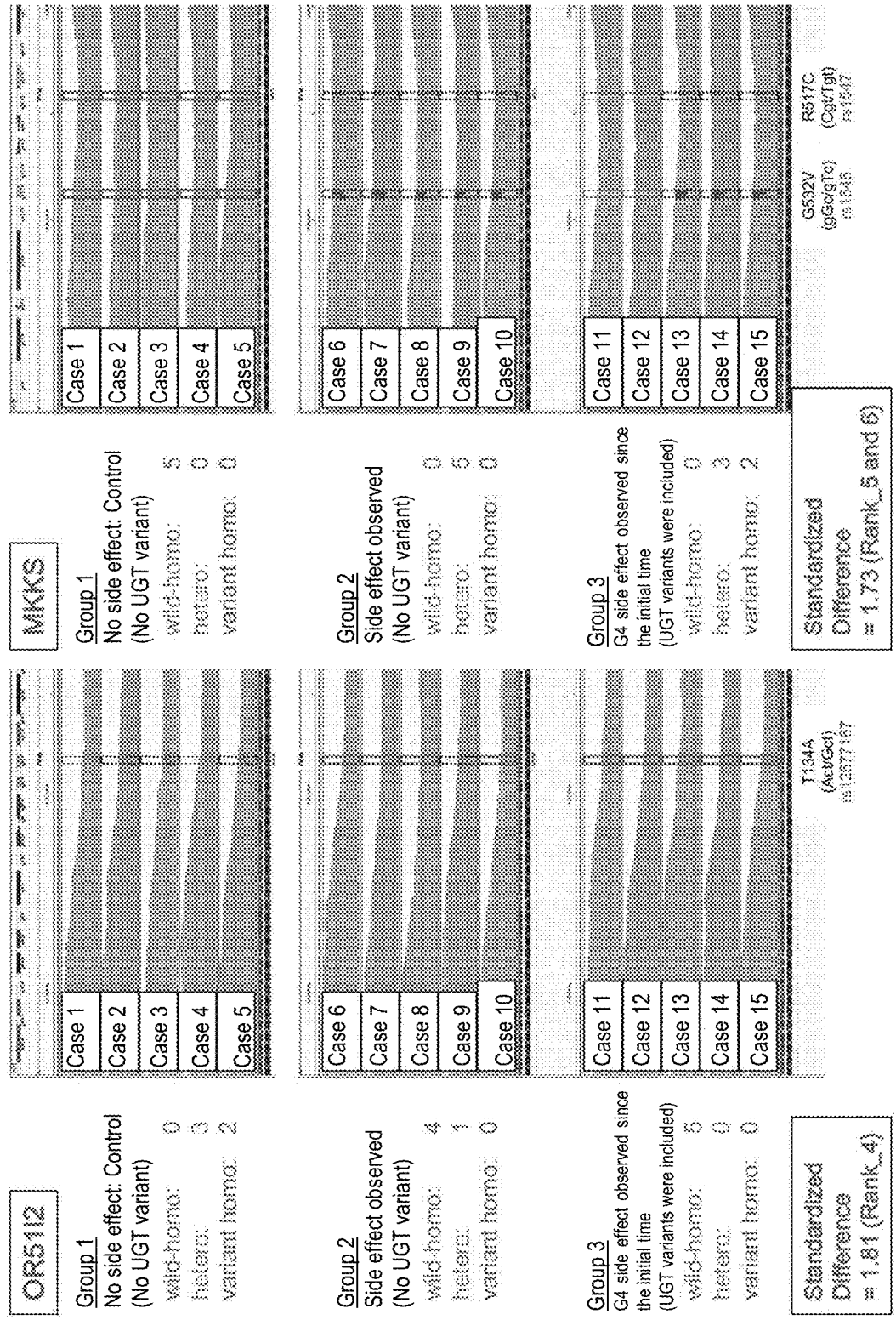
FIG. 3 is diagrams illustrating the results of subjecting the OR5I2 gene- and MKKS gene-encoding regions to exome analysis.
Figure 4:
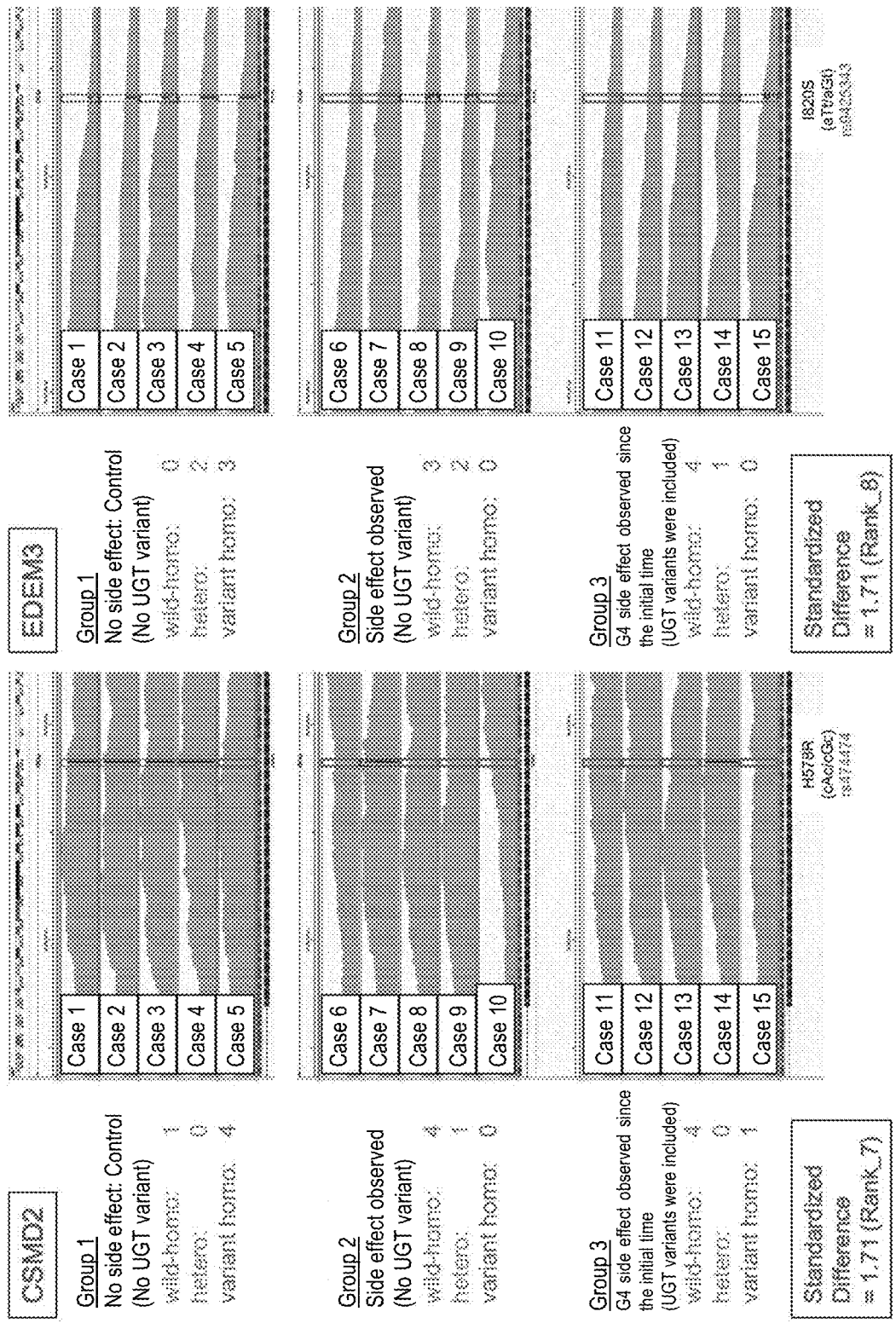
FIG. 4 is diagrams illustrating the results of subjecting the CSMD2 gene- and EDEM3 gene-encoding regions to exome analysis.

Examples of the method for assisting a prediction of a risk of occurrence of a side effect of irinotecan according to the present invention include, but are not limited to, a method for assisting a prediction of a risk of occurrence of a side effect of irinotecan by analyzing a single nucleotide polymorphism in a region encoding APCDD1L gene, R3HCC1 gene, OR5I2 gene, MKKS gene, EDEM3 gene, or ACOX1 gene which is present on genomic DNA in a biological sample collected from a test subject; or a single nucleotide polymorphism which is in linkage disequilibrium with or genetically linked to the single nucleotide polymorphism, and determining whether the single nucleotide polymorphism is homozygous for a variant type (minor allele), homozygous for a wild-type (major allele), or heterozygous. Examples of the irinotecan include a salt thereof and a solvate thereof, in particular, a hydrate thereof (e.g., CAS NO: 136572-09-3). Regarding the salt of irinotecan, it is preferable to use, as an anti-cancer agent, an acid addition salt prepared by adding a pharmaceutically acceptable acid. Examples of such an acid addition salt include: inorganic acid (e.g., hydrochloric acid, sulfuric acid, phosphoric acid, hydrobromic acid) salts; and organic acid (e.g., oxalic acid, maleic acid, fumaric acid, malic acid, tartaric acid, citric acid, benzoic acid, acetic acid, p-toluenesulfonic acid, methanesulfonic acid) salts. A hydrochloride (irinotecan hydrochloride; CAS NO:136572-09-3) can be a specific example.

The biological sample collected from a test subject has no particular limitation as long as the sample contains genomic DNA. Examples can include blood and blood-related samples therefrom (e.g., blood, serum, and plasma); body fluid such as lymph fluid, sweat, teardrops, saliva, urine, feces, ascites, and spinal fluid; and lysates and extracts of cells, a tissue, or an organ. Preferred are blood-related samples.

Examples of a preferable extraction device for extracting genomic DNA from a biological sample collected from a test subject include, but are not particularly limited to, a device for separating a DNA component directly from the biological sample to be able to purify and collect the component.

The single nucleotide polymorphism in a region encoding the APCDD1L gene (NCBI Accession number: NM 153360.1, updated in Jan. 26, 2014) is preferably a single nucleotide polymorphism present at nucleotide 186 or 238 of the nucleotide sequence encoding the APCDD1L gene and set forth in SEQ ID NO: 1 or a complementary sequence thereof. Such a single nucleotide polymorphism can be identified using an rs number (Reference SNP ID number), which is a reference number of the NCBI SNP database: www.ncbi.nlm.nih.gov/SNP, and has been registered as rs1980576 (SEQ ID NO: 7) or rs7265854 (SEQ ID NO: 8). Note that hereinafter, as used herein, a specific single nucleotide polymorphism may be described using an rs number in the above NCBI SNP database.

The single nucleotide polymorphism in a region encoding the R3HCC1 gene (NCBI Accession number: NM_001136108.1, updated in Jan. 27, 2014) is preferably a single nucleotide polymorphism present at nucleotide 358 of the nucleotide sequence encoding the R3HCC1 gene and set forth in SEQ ID NO: 2 or a complementary sequence thereof. Such a single nucleotide polymorphism has been registered as rs2272761 (SEQ ID NO: 9).

The single nucleotide polymorphism in a region encoding the OR5I2 gene (NCBI Accession number: NM_001004754.2, updated in May 16, 2014) is preferably a single nucleotide polymorphism present at nucleotide 400 of the nucleotide sequence encoding the OR5I2 gene and set forth in SEQ ID NO: 3 or a complementary sequence thereof. Such a single nucleotide polymorphism has been registered as rs12577167 (SEQ ID NO: 10).

The single nucleotide polymorphism in a region encoding the MKKS gene (NCBI Accession number: NM_018848.3, updated in May 5, 2014) is preferably a single nucleotide polymorphism present at nucleotide 1549 of the nucleotide sequence encoding the MKKS gene and set forth in SEQ ID NO: 4 or a complementary sequence thereof. Such a single nucleotide polymorphism has been registered as rs1547 (SEQ ID NO: 11).

The single nucleotide polymorphism in a region encoding the EDEM3 gene (NCBI Accession number: NM_025191.3, updated in Feb. 26, 2014) is preferably a single nucleotide polymorphism present at nucleotide 2459 of the nucleotide sequence encoding the EDEM3 gene and set forth in SEQ ID NO: 5 or a complementary sequence thereof. Such a single nucleotide polymorphism has been registered as rs9425343 (SEQ ID NO: 12).

The single nucleotide polymorphism in a region encoding the ACOX1 gene (NCBI Accession number: NM_004035.6, updated in May 5, 2014) is preferably a single nucleotide polymorphism present at nucleotide 936 of the nucleotide sequence encoding the ACOX1 gene and set forth in SEQ ID NO: 6 or a complementary sequence thereof. Such a single nucleotide polymorphism has been registered as rs1135640 (SEQ ID NO: 13).

Table 1 lists the nucleotide sequences set forth in SEQ ID NOs: 7 to 13. Each represents a complementary sequence having a single nucleotide polymorphism site and 25 nucleotides upstream and downstream of the site on the genome. In addition, the nucleotide sequences set forth in SEQ ID NO: 7 and 8, 9, 11, and 13 correspond to sequences that are complementary to the sequences of NM_153360.1, NM_001136108.1, NM_018848.3, and NM_025191.3, respectively, and each has a single nucleotide polymorphism site and 25 nucleotides upstream and downstream of the site. Note that the sequence set forth in SEQ ID NO: 7 overlaps a strand sequence that is complementary to nucleotide 347 to nucleotide 374 of the mRNA sequence (NM_153360.1) set forth in SEQ ID NO: 1. The rest 23 nucleotides (i.e., 23 nucleotides from nucleotide 25 upstream of the single nucleotide polymorphism site), which do not overlap SEQ ID NO: 1, represent an intron sequence and are thus not seen in SEQ ID NO: 1. Meanwhile, in the sequence listing, Y represents cytosine (C) or thymine (T) ([C/T]); R represents adenine (A) or guanine ([A/G/]); M represents A or C ([A/C]); and S represents C or G ([C/G]).

TABLE 1

| SEQ ID NO: 7 | rs1900576 | APCDD1L | GTCAGGATGACCTGAAGTCTTACCC[C/T]GTGGAGATCCAAGGTCCATTAAGGC |
| --- | --- | --- | --- |
| SEQ ID NO: 8 | rs7265854 | APCDD1L | TGGGCTCGAAAGAGCCGGCTGGGGT[A/G]GAAGGTGTAGGCGCGGGTCAGGAAC |
| SEQ ID NO: 9 | rs2272761 | R3HCC1 | TCCTTCTCTCCAGGCAGCTCCTCCA[C/T]GAAGGACGATGTGTCCAAATGGATC |
| SEQ ID NO: 10 | rs12577167 | OR5I2 | CATTTGTGACCCCTTGCGCTATGCA[A/G]CTGTGCTCACCACTGAAGTCATTGC |
| SEQ ID NO: 11 | rs1547 | MKKS | CAGCTTTGTGGCACAAATGGACGAC[A/G]TGTGCTTCTTAAGAAAGACCAGTTG |
| SEQ ID NO: 12 | rs9425343 | EDEM3 | ATCAACCTCCTGAGAACTTGATGAA[A/C]TCTGTTCACCACTCTGATTCTGAGA |
| SEQ ID NO: 13 | rs1135640 | ACOX1 | GCGCTGTGAGGCACCAGTCTGAAAT[C/G]AAGCCAGGGTAAGGATAGGGTCCTA |

With respect to nucleotide 186 of the nucleotide sequence encoding the APCDD1L gene and set forth in SEQ ID NO: 1, a wild-type has A and a variant type has G. With respect to nucleotide 186 of a sequence complementary to the nucleotide sequence encoding the APCDD1L gene and set forth in SEQ ID NO: 1, the wild-type has T and the variant type has C.

With respect to nucleotide 358 of the nucleotide sequence encoding the R3HCC1 gene and set forth in SEQ ID NO: 2, a wild-type has G and a variant type has A. With respect to nucleotide 358 of a sequence complementary to the nucleotide sequence encoding the R3HCC1 gene and set forth in SEQ ID NO: 2, the wild-type has C and the variant type has T.

With respect to nucleotide 400 of the nucleotide sequence encoding the OR5I2 gene and set forth in SEQ ID NO: 3, a wild-type has A and a variant type has G. With respect to nucleotide 400 of a sequence complementary to the nucleotide sequence encoding the OR5I2 gene and set forth in SEQ ID NO: 3, the wild-type has T and the variant type has C.

With respect to nucleotide 1549 of the nucleotide sequence encoding the MKKS gene and set forth in SEQ ID NO: 4, a wild-type has C and a variant type has T. With respect to nucleotide 1549 of a sequence complementary to the nucleotide sequence encoding the MKKS gene and set forth in SEQ ID NO: 4, the wild-type has G and the variant type has A.

With respect to nucleotide 2459 of the nucleotide sequence encoding the EDEM3 gene and set forth in SEQ ID NO: 5, a wild-type has T and a variant type has G. With respect to nucleotide 2459 of a sequence complementary to the nucleotide sequence encoding the EDEM3 gene and set forth in SEQ ID NO: 5, the wild-type has A and the variant type has C.

With respect to nucleotide 238 of the nucleotide sequence encoding the APCDD1L gene and set forth in SEQ ID NO: 1, a wild-type has T and a variant type has C. With respect to nucleotide 238 of a sequence complementary to the nucleotide sequence encoding the APCDD1L gene and set forth in SEQ ID NO: 1, the wild-type has A and the variant type has G.

With respect to nucleotide 936 of the nucleotide sequence encoding the ACOX1 gene and set forth in SEQ ID NO: 6, a wild-type has C and a variant type has G. With respect to nucleotide 936 of a sequence complementary to the nucleotide sequence encoding the ACOX1 gene and set forth in SEQ ID NO: 6, the wild-type has G and the variant type has C.

As used herein, the "linkage disequilibrium" means a population genetics phenomenon where in a biological population, alleles or genetic markers (polymorphisms) on genetic loci are associated with one another in a non-random manner, that is, the frequency of a specific combination (haplotype) is significantly higher. The wording "genetically linked to" means a genetics phenomenon where a combination of specific alleles is genetically transmitted from parent to offspring not in accordance with the Mendelian laws.

As used herein, examples of the side effects can include, but are not limited to, leucopenia, neutropenia, diarrhea, vomiting, systemic malaise, anorexia, and alopecia. Preferred examples can include leucopenia and neutropenia.

As used herein, any publicly known method for analyzing a single nucleotide polymorphism can be used as the method for analyzing a single nucleotide polymorphism. Examples of the method can include a real-time PCR method, direct sequencing, a TaqMan (R) PCR method, an Invader (R) method, a Luminex (R) method, a quenching primer/probe (QP) method, MALDI-TOF mass spectrometry, and a molecular beacon method. Specific examples can include: a method comprising performing an amplifying reaction using, as a template, genomic DNA of a biological sample collected from a test subject (usually a human test subject) to amplify, using the PCR using primers, a nucleic acid fragment containing a single nucleotide polymorphism of interest, and detecting hybridization between the resulting nucleic acid fragment and a pair of probes corresponding to wild and variant types; and a method comprising detecting a wild-type or a variant type by using, during the above PCR amplification process, a probe specific to the single nucleotide polymorphism.

As the present probe used in the above method for analyzing a single nucleotide polymorphism, any probe may be allowed which consists of an oligonucleotide that hybridizes, under a stringent condition, with sequence of 5 to 50 consecutive nucleotides containing a single nucleotide polymorphism of interest. Examples can include probes, each consisting of an oligonucleotide that hybridizes, under a stringent condition, with a sequence that contains 5 to 50 consecutive nucleotides, preferably 10 to 40 nucleotides, and more preferably 15 to 30 nucleotides and contains: a single nucleotide polymorphism site present at nucleotide 186 of the nucleotide sequence encoding the APCDD1L gene and set forth in SEQ ID NO: 1 or a complementary sequence thereof; a single nucleotide polymorphism site present at nucleotide 358 of the nucleotide sequence encoding the R3HCC1 gene and set forth in SEQ ID NO: 2 or a complementary sequence thereof; a single nucleotide polymorphism site present at nucleotide 400 of the nucleotide sequence encoding the OR51I2 gene and set forth in SEQ ID NO: 3 or a complementary sequence thereof; a single nucleotide polymorphism site present at nucleotide 1549 of the nucleotide sequence encoding the MKKS gene and set forth in SEQ ID NO: 4 or a complementary sequence thereof; a single nucleotide polymorphism site present at nucleotide 2459 of the nucleotide sequence encoding the EDEM3 gene and set forth in SEQ ID NO: 5 or a complementary sequence thereof; a single nucleotide polymorphism site present at nucleotide 238 of the nucleotide sequence encoding the APCDD1L gene and set forth in SEQ ID NO: 1 or a complementary sequence thereof; or a single nucleotide polymorphism site present at nucleotide 936 of the nucleotide sequence encoding the ACOX1 gene and set forth in SEQ ID NO: 6 or a complementary sequence thereof. In addition, when an oligonucleotide probe which is synthesized using a synthetic nucleic acid such as Locked Nucleic Acid (LNA) is used as a probe, this probe can be specifically hybridized even with a short nucleotide sequence.

As used herein, the term "under a stringent condition" refers to a condition under which there is what is called specific hybridization formed and there is no non-specific hybridization formed. Specific examples can include: a condition in which hybridization is carried out at 45° C. in a solution containing 6×SSC (10×SSC is a solution containing 1.5 M NaCl and 0.15 M trisodium citrate) and 50% formamide, followed by washing using 2×SSC at 50° C. (Molecular Biology, John Wiley & Sons, N. Y. (1989), 6.3.1-6.3.6); and a condition in which hybridization is carried out at 54° C. in a solution containing 3×SSC/0.3× SDS, followed by washing using, in sequence, a washing solution A (10×SSC/1% SDS solution), a washing solution B (20×SSC), and a washing solution C (5×SSC) (see Patent Document 2).

Meanwhile, a probe according to the present invention may be immobilized on a support. Examples of the support can include flat substrates and bead-like spherical supports. Specific examples can include the support described in Patent Document 2. In addition, a probe for detecting a wild-type and a probe for detecting a variant type may be immobilized on the same support or different supports.

As the present primer used in the above method for analyzing a single nucleotide polymorphism, any primer may be allowed which consists of an oligonucleotide that can amplify, using genomic DNA as a template, an at least five-nucleotide fragment containing a single nucleotide polymorphism site of interest. Examples can include primers, each containing an oligonucleotide that can amplify at least 5, preferably 10 to 500, more preferably 20 to 200, and still more preferably 50 to 100 consecutive nucleotides containing: a single nucleotide polymorphism site present at nucleotide 186 of the nucleotide sequence encoding the APCDD1L gene and set forth in SEQ ID NO: 1; a single nucleotide polymorphism site present at nucleotide 358 of the nucleotide sequence encoding the R3HCC1 gene and set forth in SEQ ID NO: 2; a single nucleotide polymorphism site present at nucleotide 400 of the nucleotide sequence encoding the OR51I2 gene and set forth in SEQ ID NO: 3; a single nucleotide polymorphism site present at nucleotide 1549 of the nucleotide sequence encoding the MKKS gene and set forth in SEQ ID NO: 4; a single nucleotide polymorphism site present at nucleotide 2459 of the nucleotide sequence encoding the EDEM3 gene and set forth in SEQ ID NO: 5; a single nucleotide polymorphism site present at nucleotide 238 of the nucleotide sequence encoding the APCDD1L gene and set forth in SEQ ID NO: 1; or a single nucleotide polymorphism site present at nucleotide 936 of the nucleotide sequence encoding the ACOX1 gene and set forth in SEQ ID NO: 6.

Use of a previously labeled primer or use of labeled nucleotides as substrates for an amplification reaction when the at least five consecutive nucleotides containing a single nucleotide polymorphism site of interest are amplified makes the resulting amplification product distinguishable. Examples of the label can include, but are not particularly limited to, radioactive isotopes, fluorescent dyes, and organic compounds such as digoxigenin (DIG) and biotin.

The above probes and primers can be obtained through chemical synthesis using a nucleic acid synthesizer. Examples of the nucleic acid synthesizer used can include a DNA synthesizer and a full-automatic nucleic acid synthesizer.

When the amplified nucleic acid fragment has a label, the label may be detected to evaluate a nucleic acid fragment hybridized with each probe. For example, when a fluorescent dye is used as the label, a nucleic acid fragment hybridized with a probe can be evaluated by measuring the levels of fluorescence derived from the fluorescent dye. Specifically, calculated is a ratio of a nucleic acid fragment hybridized with a probe for detecting a wild-type to a nucleic acid fragment hybridized with a probe for detecting a variant type. This calculation can be executed by using an output value when a label of the probe for detecting a wild-type is detected and an output value when a label of the probe for detecting a variant type is detected.

A reference value can be calculated by dividing the intensity derived from the nucleic acid fragment hybridized with the probe for a variant type by the average of the intensities derived from the nucleic acid fragment hybridized with the probe for a variant type and from the nucleic acid fragment hybridized with the probe for a wild-type. This reference value is an approximate value obtained by normalizing the existing amount of a variant type included in a nucleic acid fragment. Accordingly, it can be determined from the level of this reference value whether a single nucleotide polymorphism is homozygous for a variant type, homozygous for a wild-type, or heterozygous, by analyzing the single nucleotide polymorphism of a test subject.

When this reference value is used, as it is determined whether a single nucleotide polymorphism is homozygous for a variant type, homozygous for a wild-type, or heterozygous by analyzing the single nucleotide polymorphism of a test subject, it is preferable to preset two different thresholds (threshold A and threshold B). Note that the threshold A and the threshold B herein have a relationship: threshold A>threshold B. Specifically, the determination can be given as follows: when the reference value as so calculated exceeds threshold A, the single nucleotide polymorphism is homozygous for a variant type; when the reference value is threshold A or less and exceeds threshold B, the single nucleotide polymorphism is heterozygous; and when the reference value is threshold B or less, the single nucleotide polymorphism is homozygous for a wild-type.

These threshold A and threshold B are prescribed with respect to each of the above-mentioned single nucleotide polymorphisms. Examples of the method for prescribing threshold A and threshold B can include, but are not limited to, a method comprising: calculating, as described above, a reference value by using a sample, the genotype of which has already been known; and calculating a normalized probability density for each of the cases where the single nucleotide polymorphism is homozygous for the variant type, where the single nucleotide polymorphism is homozygous for the wild-type, and where the single nucleotide polymorphism is heterozygous. At this time, an intersection between the probability densities (i.e., a position where the level of one probability density becomes higher or lower than the level of the other and which is between their maximal peaks) is determined; and the average values are each calculated for the case where the single nucleotide polymorphism is homozygous for the variant type, the case where the single nucleotide polymorphism is homozygous for the wild-type, or the case where the single nucleotide polymorphism is heterozygous. Then, the threshold between the case where the single nucleotide polymorphism is homozygous for the variant type and the case where the single nucleotide polymorphism is heterozygous can be calculated by averaging the value at the intersection and the average of (the average when the single nucleotide polymorphism is homozygous for the variant type and the average when the single nucleotide polymorphism is heterozygous). Likewise, the threshold between the case where the single nucleotide polymorphism is heterozygous and the case where the single nucleotide polymorphism is homozygous for the wild-type can be calculated by averaging the value at the intersection and the average of (the average when the single nucleotide polymorphism is heterozygous and the average when the single nucleotide polymorphism is homozygous for the wild-type).

The above method may be used to assist a prediction of a risk of occurrence of a side effect of irinotecan by analyzing: a single nucleotide polymorphism in a region encoding the APCDD1L gene, the R3HCC1 gene, the OR5I2 gene, the MKKS gene, the EDEM3 gene, or the ACOX1 gene; or a single nucleotide polymorphism which is in linkage disequilibrium with or genetically linked to the single nucleotide polymorphism, and determining whether a single nucleotide polymorphism is homozygous for a variant type, homozygous for a wild-type, or heterozygous. For example, first, a single nucleotide polymorphism in a region encoding the APCDD1L gene, the R3HCC1 gene, the OR5I2 gene, the MKKS gene, the EDEM3 gene, or the ACOX1 gene or a single nucleotide polymorphism which is in linkage disequilibrium with or genetically linked to the former single nucleotide polymorphism is correlated between patients with the occurrence of a side effect of irinotecan and patients without it. Next, the single nucleotide polymorphism of patients of interest is examined and compared to data of the pre-examined patients, so that the prediction of the risk of the occurrence of a side effect of irinotecan can be assisted among the patients of interest.

Specifically, it is possible to help predict that when the single nucleotide polymorphism is homozygous for a variant type with respect to each of at least one, preferably at least two, and more preferably three single nucleotide polymorphisms selected from the above (a), (b), and (d) and/or when the single nucleotide polymorphism is homozygous for a wild-type with respect to each of at least one, preferably at least two, more preferably at least three, and most preferably four single nucleotide polymorphisms selected from (c), (e), (f), and (g), the risk of the occurrence of a side effect of irinotecan is high. By contrast, it is possible to help predict that when the single nucleotide polymorphism is homozygous for a wild-type with respect to each of at least one, preferably at least two, and more preferably three single nucleotide polymorphisms selected from the above (a), (b), and (d) and/or when the single nucleotide polymorphism is homozygous for a variant type with respect to each of at least one, preferably at least two, more preferably at least three, and most preferably four single nucleotide polymorphisms selected from (c), (e), (f), and (g), the risk of the occurrence of a side effect of irinotecan is low.

Further, it is also possible to help predict that when the single nucleotide polymorphism is heterozygous with respect to all of at least two, preferably at least three, more preferably at least five, and still more preferably seven single nucleotide polymorphisms selected from the above (a) to (g), the risk of the occurrence of a side effect of irinotecan is high.

A kit for assisting the prediction of the risk of the occurrence of a side effect of irinotecan according to the present invention has no particular limitation as long as the kit contains a probe or primer according to the present invention. The kit may further contain a reagent such as a buffer and an enzyme for analyzing a single nucleotide polymorphism and/or a package insert for describing how to help predict that the risk of the occurrence of a side effect of irinotecan is high.

EXAMPLES

Example 1

[Search for an Irinotecan-Side-Effect-Related Factor]

A serious side effect of irinotecan can be sometimes observed even in patients without any UGT1A gene polymorphism (at 7 sites including UGT1A1*6, *27, *28, UGT1A7 (387T>G, 622T>C), UGT1A9*1b, UGT1A1*60) related to the side effect. Here, the following method was used to search for a novel irinotecan-side-effect-related factor.

(Subjects Analyzed)

A next-generation sequencer was used to perform exome analysis by using genomic DNA prepared from peripheral blood of: a case group (Group 1; n=5), as a control group, in which all the above-mentioned 7 different polymorphisms were genotypes having a low risk of the side effect and no side effect was observed; a case group (Group 2; n=5) in which all the 7 different polymorphisms of the above UGT1A gene were genotypes having a low risk of the side effect, but the side effect (Grade 3: leucopenia, neutropenia) was observed; and a case group (Group 3; n=5) being heterozygous for any one of the above 7 different polymorphisms and a very serious side effect (Grade 4: leucopenia, neutropenia) was observed since the initial administration, as case groups. Note that all case groups consisted of Japanese test subjects.

Preparation of Genomic DNA

Genomic DNA was prepared, by a sodium iodide method (Wang et al., Nucleic Acids Res 34: 195-201 (2014)), using a subject's peripheral blood which had been collected into an EDTA-containing tube. The prepared DNA was dissolved in 10 mM Tris-HCl buffer solution (pH 8.0) containing 1 mM EDTA·2Na and was stored at 4° C. or −20° C. until the next use.

(Exome Analysis Using Next-Generation Sequencer)

The following method was used for exome analysis using a next-generation sequencer. First, the concentration of the prepared genomic DNA was quantified from absorbance obtained using a spectrophotometer (Nanodrop (R); manufactured by Scrum Inc.). Next, the genomic DNA was subjected to agarose gel electrophoresis to test the quality. Then, an acoustic solubilizer (manufactured by Covaris Inc.) was used to fragment the genomic DNA into 150- to 200-bp fragments, and adopters were ligated thereto. Then, the fragmented genomic DNA was subjected to PCR amplification and the resulting products were hybridized with a SureSelect (R) Oligo Capture library (manufactured by Agilent Technologies, Inc.), and collected using streptavidin magnetic beads and then concentrated. The collected DNA library was used as a template and index-attached primers were used to perform PCR amplification to give an index-attached sequence library. The quality of the prepared sequence library was evaluated using an Agilent 2100 Bioanalyzer (manufactured by Agilent Technologies, Inc.). The resulting sequence library was analyzed using a HiSeq 2000 (manufactured by Illumina, Inc.) to give template DNA nucleotide sequences. Clean read sequences were extracted from the resulting nucleotide sequences and were mapped on reference sequences (UCSC hg19: a human reference genome) by using Burrows-Wheeler Aligner (BWA) (0.7.12).

Then, from the respective gene polymorphisms of each sample as obtained from the exome analysis, gene polymorphisms were extracted using a Genome Analysis Toolkit (GATK) (3.4-46). Further, the polymorphisms were annotated (e.g., an amino acid sequence was affected) by using SnpEff (v4.1k). Each gene polymorphism that could affect an amino acid sequence was extracted based on the results of SnpEff, sorts intolerant from tolerant (SIFT), and polymorphism phenotyping (PolyPhen). The differences between the control group and the case groups were ranked using a standardized difference (d) calculated using the following equation (I). In the equation, $P_T$ represents the proportion of an allele with a gene polymorphism of interest in a case (test) group and $P_C$ represents the proportion of the allele with a gene polymorphism of interest in the control group.

$$d=|P_T-P_C|/\text{SQRT}[\{P_T\times(1-P_T)+(P_C\times(1-P_C)\}/2] \quad \text{Equation (I)}$$

Figure 6:
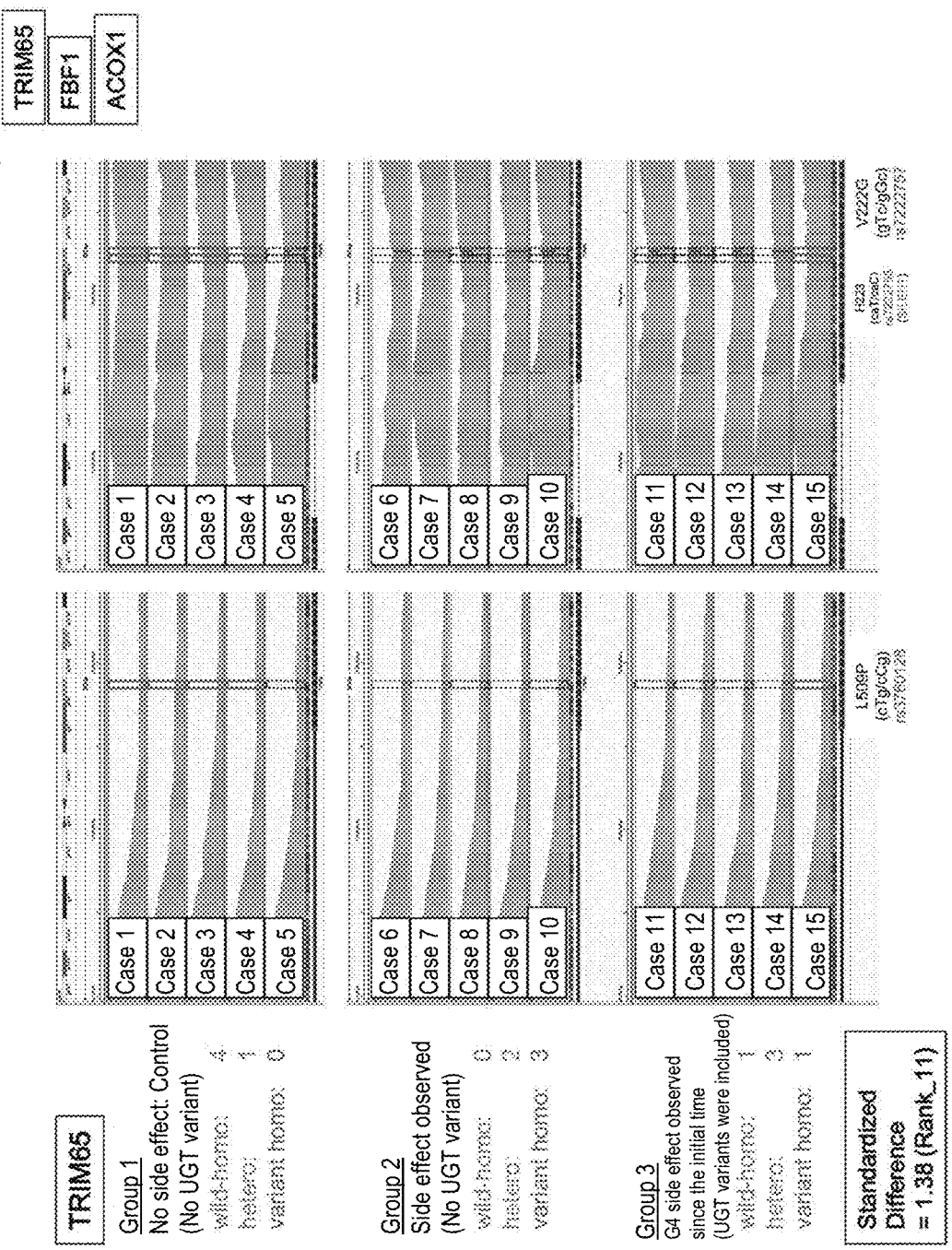
FIG. 6 is diagrams illustrating the results of subjecting the TRIM65 gene-encoding region to exome analysis.
Figure 7:
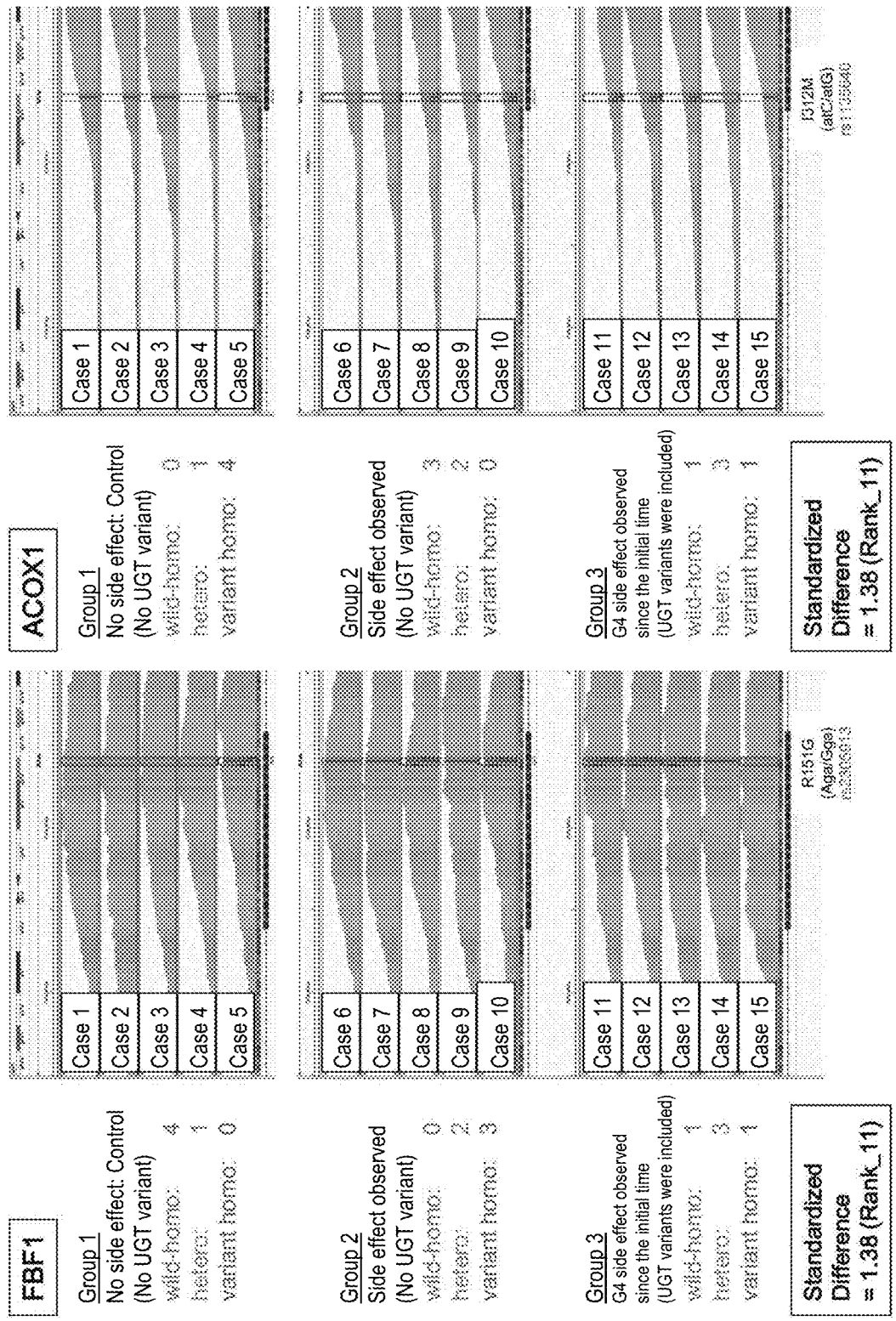
FIG. 7 is diagrams illustrating the results of subjecting the FBF1 gene- and ACOX1 gene-encoding regions to exome analysis.

The resulting candidates for irinotecan-side-effect-related factor were single nucleotide polymorphisms including: single nucleotide polymorphisms rs3946003, rs1980576, and rs7265854 in a region encoding the APCDD1L gene; single nucleotide polymorphisms rs2272761, rs2272762, and rs13530 in a region encoding the R3HCC1 gene; a single nucleotide polymorphism rs12577167 in a region encoding the OR51I2 gene; single nucleotide polymorphisms rs1545 and rs1547 in a region encoding the MKKS gene; a single nucleotide polymorphism rs474474 in a region encoding the CSMD2 gene; a single nucleotide polymorphism rs9425343 in a region encoding the EDEM3 gene; a single nucleotide polymorphism rs2335052 in a region encoding the GATA2 gene; single nucleotide polymorphisms rs3760128, rs7222755, and rs7222757 in a region encoding the TRIM65 gene; a single nucleotide polymorphism rs2305913 in a region encoding the FBF1 gene; and a single nucleotide polymorphism rs1135640 in a region encoding the ACOX1 gene. The results of exome analysis of the respective genes were visualized by Integrative Genomics Viewer software (IGV; manufactured by the Broad Institute) and are shown in FIGS. 1 to 7. In the figures, the positions of the single nucleotide polymorphisms are boxed; the bold line indicates a case where the single nucleotide polymorphism is homozygous for a wild-type; the dotted line indicates a case where the single nucleotide polymorphism is heterozygous; and the thin line indicates a case where the single nucleotide polymorphism is homozygous for a variant type. In addition, in this Example, complete linkage was observed between rs1980576 and rs3946003 (FIG. 1), between rs2272761 and rs2272762 and rs13530 (FIG. 2), between rs1545 and rs1547 (FIG. 3), and between rs1135640 and rs3760128, rs7222755, rs7222757, and rs2305913 (FIGS. 6 and 7).

Example 2

[Examining Results of Exome Analysis]
(Methodology for Examining Results of Exome Analysis)

By using a TaqMan (R) probe method, clinical samples from 75 Japanese patients with colon cancer who had received irinotecan were further examined with respect to: among the candidates for irinotecan-side-effect-related factor as obtained from the results of Example 1, a single nucleotide polymorphism rs1980576 in a region encoding the APCDD1L gene; a single nucleotide polymorphism rs2272761 in a region encoding the R3HCC1 gene; a single nucleotide polymorphism rs12577167 in a region encoding the OR51I2 gene; a single nucleotide polymorphism rs1547 in a region encoding the MKKS gene; a single nucleotide polymorphism rs9425343 in a region encoding the EDEM3 gene; a single nucleotide polymorphism rs7265854 in a region encoding the APCDD1L gene; and a single nucleotide polymorphism rs1135640 in a region encoding the ACOX1 gene. By using TaqMan SNP Assays Human (manufactured by Applied Biosystems, Inc.) and LightCycler (R) 480 Probe Master (manufactured by Roche Diagnostics, Inc.), Universal ProbeLibrary (manufactured by Roche Diagnostics, Inc.), and LightCycler 480 System II (manufactured by Roche Diagnostics, Inc.), 10 ng of genomic DNA was subjected to genotyping. After incubation at 95° C. for 10 min, the sample was subjected to PCR amplification with 55 cycles for rs1980576, rs2272761, and rs9425343, 45 cycles for rs12577167, rs7265854, and rs1135640, or 40 cycles for rs1547 (1 cycle consisted of 92° C. for 15 sec and 60° C. for 60 sec). The fluorescence emitted from the PCR products were measured.

(Results)

Figure 8:
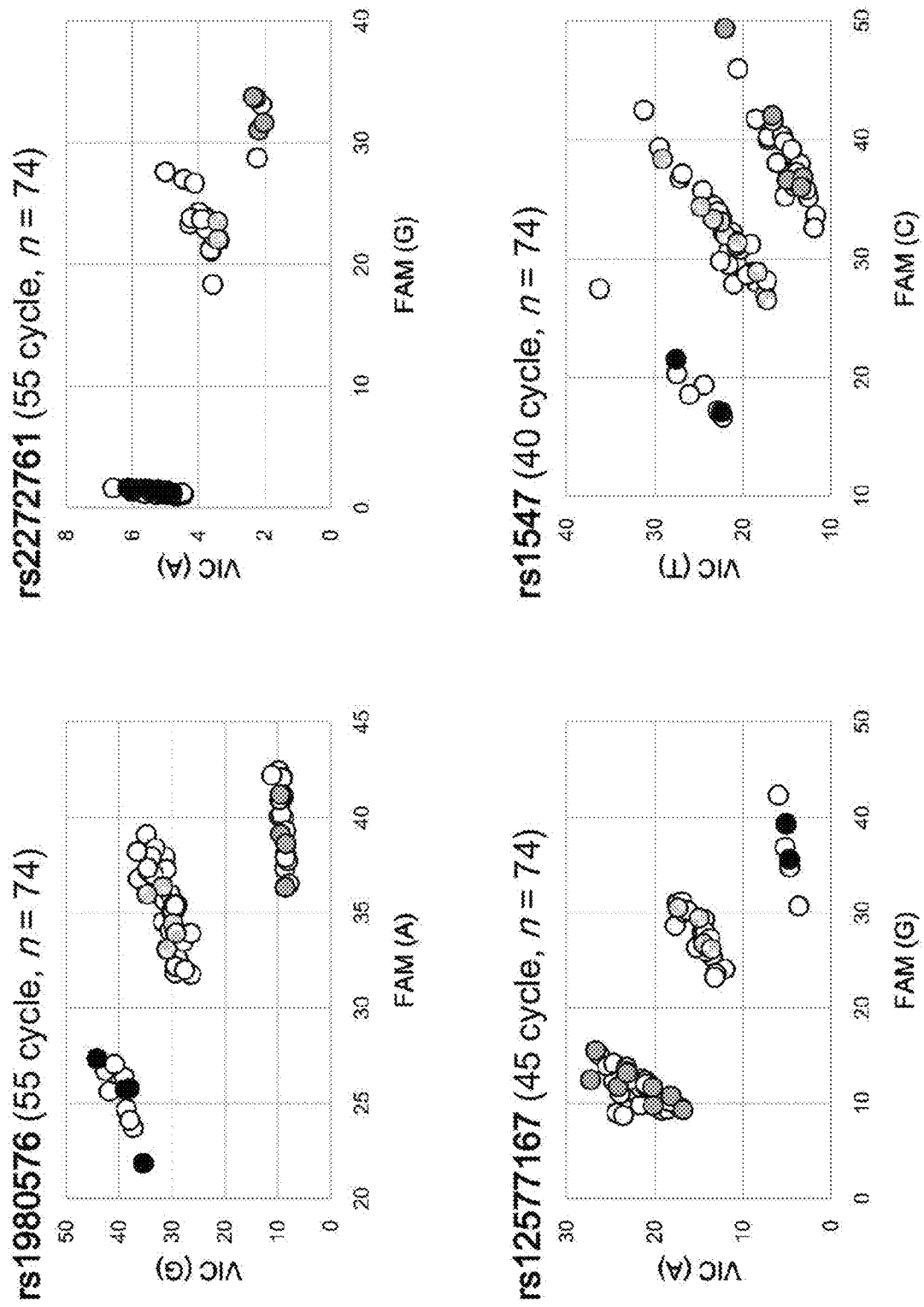
FIG. 8 is graphs illustrating the results of analyzing, using a TaqMan probe method, a single nucleotide polymorphism rs1980576 in a region encoding the APCDD1L gene, a single nucleotide polymorphism rs2272761 in a region encoding the R3HCC1 gene, a single nucleotide polymorphism rs12577167 in a region encoding the OR5I2 gene, and a single nucleotide polymorphism rs1547 in a region encoding the MKKS gene.
Figure 9:
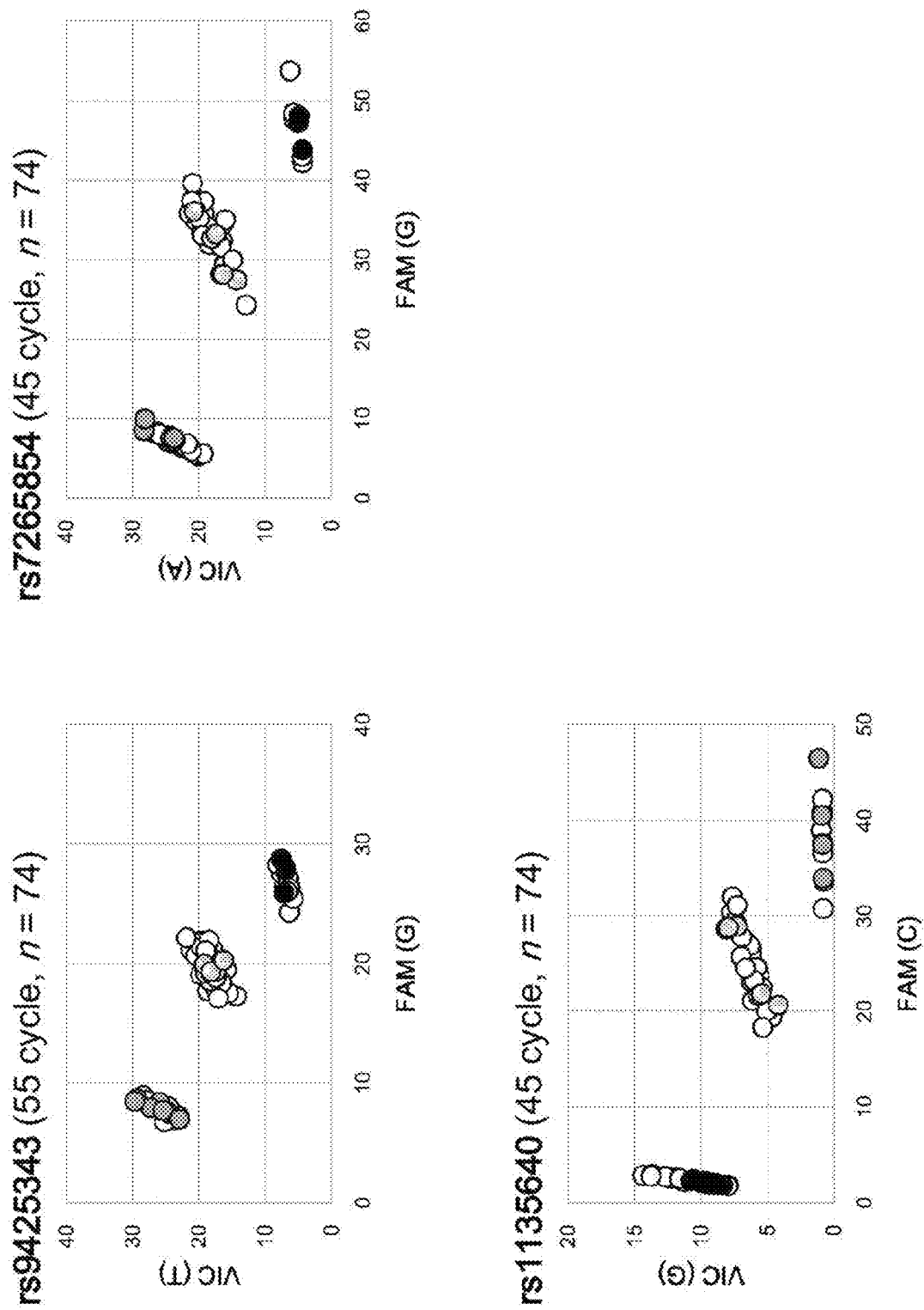
FIG. 9 is graphs illustrating the results of analyzing, using a TaqMan probe method, a single nucleotide polymorphism rs9425343 in a region encoding the EDEM3 gene, a single nucleotide polymorphism rs7265854 in a region encoding the APCDD1L gene, and a single nucleotide polymorphism rs1135640 in a region encoding the ACOX1 gene.

FIGS. 8 and 9 show the analysis results obtained by the above TaqMan probe method. Since only 74 cases were analyzed with respect to rs1135640, 74 cases were analyzed with respect to all the genotypes and the analysis results are shown in FIGS. 8 and 9. The abscissa and the ordinate represent the levels of fluorescence emitted from a fluorescently labeled (FAM and VIC, respectively) probe specific to each allele. The black circles, the deep gray circles, and the light gray (dotty) circles represent a case where the single nucleotide polymorphism was homozygous for a variant type, a case where the single nucleotide polymorphism was homozygous for a wild-type, and a case where the single nucleotide polymorphism was heterozygous, respectively, as revealed by exome analysis. The white circles represent a case where exome analysis was not conducted. FIGS. 8 and 9 demonstrated that the genotypes were clearly distinguishable when the TaqMan probe method was used. Also, the results of exome analysis were reproduced by the TaqMan probe method.

Example 3

Figure 10:
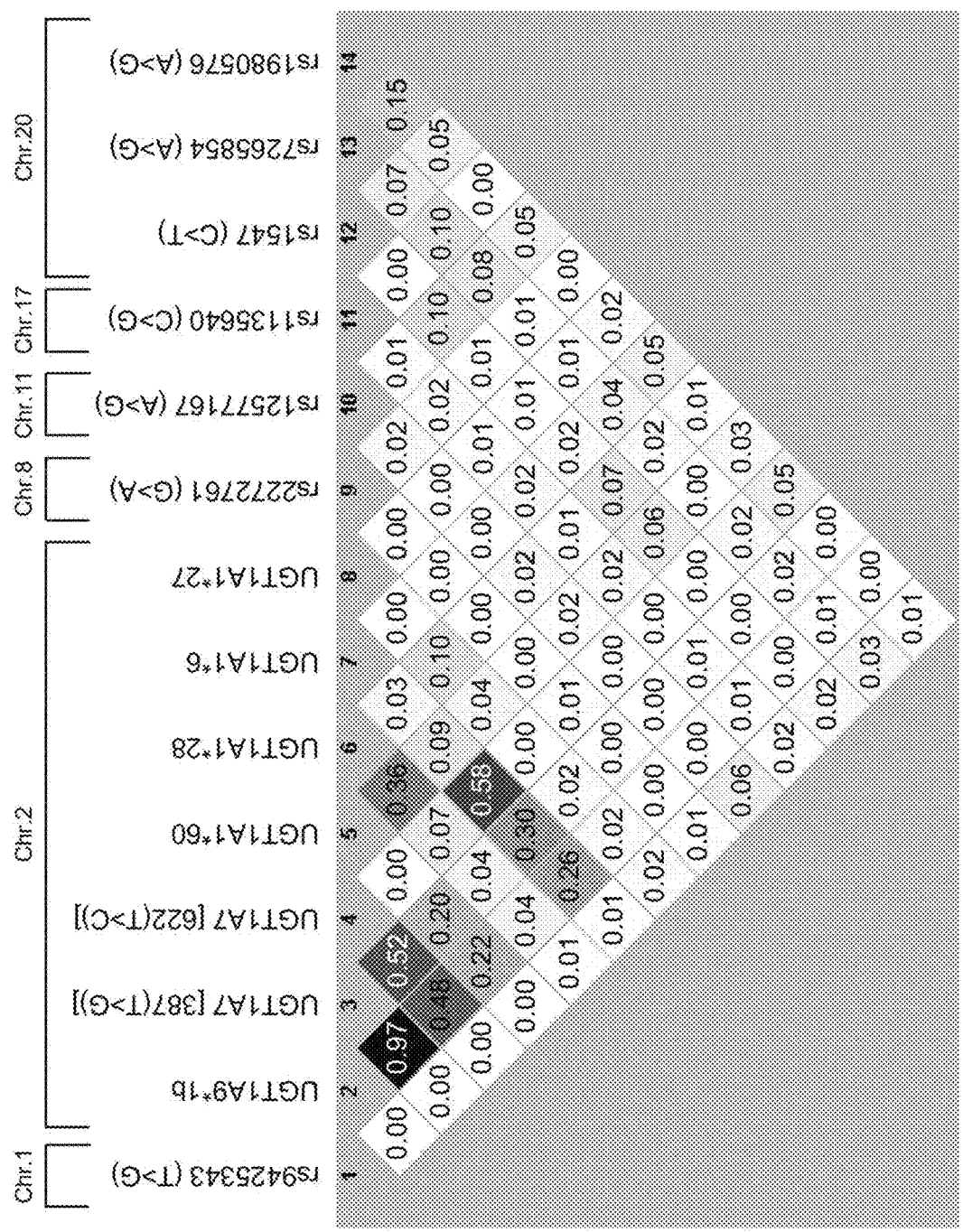
FIG. 10 is a diagram illustrating the results of subjecting rs9425343, rs2272761, rs12577167, rs1135640, rs1547, rs7265854, rs1980576, and UGT1A gene polymorphisms to linkage disequilibrium analysis and LD analysis.

[Linkage to UGT1A Gene Mutations]
Regarding the 74 cases in Example 2, the TaqMan probe method and direct sequencing were used to determine the genotype of each of the UGT genes, namely UGT1A gene polymorphisms including UGT1A9*1b, UGT [387], UGT [622], UGT1A1*60, UGT1A1*28, UGT1A1*6 and UGT1A1*27, as well as to determine the genotype of rs9425343, rs2272761, rs12577167, rs1135640, rs1547, rs7265854, or rs1980576. Further, linkage disequilibrium analysis and LD analysis were conducted using Haploview 4.2 software. The results are shown in FIG. 10. In FIG. 10, the numbers indicate correlation coefficients ($r^2$). As shown in FIG. 10, the UGT1A gene polymorphisms were not linked to (associated with) rs9425343, rs2272761, rs12577167, rs1135640, rs1547, rs7265854, or rs1980576. In addition, no linkage was observed among rs9425343, rs2272761, rs12577167, rs1135640, rs1547, rs7265854, and rs1980576. This clearly demonstrated that these single nucleotide polymorphisms (marker sites) can be used auxiliary in the method for assisting a prediction of a risk of occurrence of a side effect of irinotecan.

Example 4

Table 2 shows the relationship between each mutation and the incidence of a side effect (hematologic toxicity: Toxicity) in 68 cases, in which UGT1A1*6 (homozygous) (2 cases), UGT1A1*28 (homozygous) (2 cases), and UGT1A1*6 (heterozygous) and *28 (heterozygous) (3 cases) were excluded from the 75 cases in Example 2. Table 2 shows P values (P value/C.-A.) as the results of a Cochran-Armitage trend test. Further, Table 3 shows the results of performing a Fisher's exact test on 67 cases in which 1 case was excluded from the above 68 cases. The "Odds ratio" in Table 3 refers to an odds ratio indicating the occurrence of a side effect as calculated using a Fisher's exact test on a single nucleotide polymorphism being homozygous for a wild-type or homozygous for a variant type.

TABLE 2

Statistical analysis in cases (N = 68) where subjects who were homozygous for UGT1A1*28, homozygous for *6, or compound heterozygous were excluded.

| Rank (st. dif.) | | Toxicity | | | P value |
| | | Yes | No | (% of Yes) | C.-A.** |
| --- | --- | --- | --- | --- | --- |
| Rank_1 (2.16) | APCDD1L; rs1980576 (A > G): an alternative for rs3946003 as revealed by exome analysis | | | | |
| | A/A | 5 | 16 | (23.8) | 0.008 |
| | A/G | 16 | 20 | (44.4) | |
| | G/G | 8 | 3 | (72.7) | |
| Rank_2, 3 (1.98) | R3HCC1; rs2272761 (G > A): linked to rs13530 as revealed by exome analysis | | | | |
| | G/G | 0 | 6 | (0.0) | 0.049 |
| | G/A | 8 | 11 | (42.1) | |
| | A/A | 21 | 22 | (48.8) | |
| Rank_4 (1.81) | OR5112; rs12577167 (A > G) | | | | |
| | A/A | 20 | 19 | (51.3) | 0.052 |
| | A/G | 8 | 14 | (36.4) | |
| | G/G | 1 | 6 | (14.3) | |

TABLE 2-continued

Statistical analysis in cases (N = 68) where subjects who were homozygous for UGT1A1*28, homozygous for *6, or compound heterozygous were excluded.

| Rank (st. dif.) | | Toxicity | | | P value |
| | | Yes | No | (% of Yes) | C.-A.** |
| --- | --- | --- | --- | --- | --- |
| Rank_5, 6 (1.73) | MKKS; rs1547 (C > T): linked to rs1545 as revealed by exome analysis | | | | |
| | C/C | 8 | 20 | (28.6) | 0.042 |
| | C/T | 16 | 16 | (50.0) | |
| | T/T | 5 | 3 | (62.5) | |
| Rank_7 (1.71) | CSMD2; rs474474 (A > G) | | | | |
| | A/A | 17 | 16 | (51.5) | 0.334 |
| | A/G | 8 | 18 | (30.8) | |
| | G/G | 4 | 5 | (44.4) | |
| Rank_8 (1.71) | EDEM3; rs9425343 (T > G) | | | | |
| | T/T | 12 | 8 | (60.0) | 0.032 |
| | T/G | 14 | 21 | (40.0) | |
| | G/G | 3 | 10 | (23.1) | |
| Rank_9 (1.71) | GATA2; rs2335052 (G > A) | | | | |
| | G/G | 16 | 14 | (53.3) | 0.188 |
| | G/A | 10 | 20 | (33.3) | |
| | A/A | 3 | 5 | (37.5) | |
| Rank_10 (1.50) | APCDD1L; rs7268854 (A > G) | | | | |
| | A/A | 13 | 13 | (50.0) | 0.083 |
| | A/G | 15 | 18 | (45.5) | |
| | G/G | 1 | 8 | (11.1) | |
| Rank_11 (1.38) | ACOX1; rs1135640 (C > G)***; N = 67 | | | | |
| | C/C | 6 | 3 | (66.7) | 0.018 |
| | C/G | 15 | 14 | (51.7) | |
| | G/G | 8 | 21 | (27.6) | |

**Cochran-Armitage trend test.
***Exome analysis (N = 15) revealed linkage to TRIM65 (rs3760128), TRIM65 (rs7222757), and FBF1 (rs2305913).

TABLE 3

N = 67 (subjects who were homozygous for UGT1A1*28, homozygous for *6, or compound heterozygous were excluded)

| | | Toxicity | | | Fisher's Exact Test | |
| | | Yes | No | (% of Yes) | P value | Odds ratio |
| --- | --- | --- | --- | --- | --- | --- |
| Rank_1 | APCDD1L; rs1980576 (A > G): an alternative for rs3946003 as revealed by exome analysis | | | | | |
| | A/A | 5 | 16 | (23.8) | 0.036 | 0.292 |
| | A/G, G/G | 24 | 22 | (52.2) | | |
| | A/A, A/G | 21 | 35 | (37.5) | | |
| | G/G | 8 | 3 | (72.7) | 0.046 | 4.344 |
| Rank_2, 3 | R3HCC1; rs2272761 (G > A): linked to rs13530 as revealed by exome analysis | | | | | |
| | G/G | 0 | 6 | (0.0) | 0.032 | 0.000 |
| | G/A, A/A | 29 | 32 | (47.5) | | |
| | | EDEM3; rs9425343 (T > G) | | | | |
| | T/T | 12 | 7 | (63.2) | 0.056 | 3.070 |
| | T/G, G/G | 17 | 31 | (35.4) | | |
| Rank_10 | APCDD1L; rs7265854 (T > C) | | | | | |
| | T/T, T/C | 28 | 30 | (48.3) | | |
| | C/C | 1 | 8 | (11.1) | 0.0667 | 0.1372 |
| Rank_11 | ACOX1; rs1135640 (C > G)*** | | | | | |
| | C/C, C/G | 21 | 17 | (55.3) | | |
| | G/G | 8 | 21 | (27.6) | 0.028 | 0.314 |

***Exome analysis (N = 15) revealed linkage to TRIM65 (rs3760128), TRIM65 (rs7222757), and FBF1 (rs2305913).

Table 2 shows that an irinotecan side effect was observed in 42.6% cases (29 cases) of 68 cases where the subjects had been considered to have a low risk of a side effect in view of the UGT1A gene polymorphisms conventionally used to determine the risk of a side effect of irinotecan. Meanwhile, the occurrence of rs1980576, rs2272761, rs1547, rs9425343, or rs1135640 tended to be significantly proportional to the incidence of a side effect of irinotecan in cases where the subjects had been considered to have a low risk of a side effect in view of the UGT1A gene polymorphisms. In addition, Table 3 revealed that not even a single case where the single nucleotide polymorphism was homozygous for a wild-type (G/G) with respect to rs2272761 exhibited hematologic toxicity.

Next, Table 4 shows the relationship between each polymorphism and the incidence of a side effect (hematologic toxicity: Toxicity) in 73 cases, in which UGT1A1*6 (homozygous) (2 cases) were excluded from the 75 cases in Example 2. The term (P value/C.-A.) in Table 4 is the same as in Table 2. Further, Table 5 shows the results of performing a Fisher's exact test on 72 cases in which 1 case was excluded from the above 73 cases. The term "Odds ratio" in Table 5 is the same as in Table 3.

TABLE 4

Statistical analysis in cases (N = 73) where subjects who were homozygous for UGT1A1*28 and received a reduced amount of irinotecan were excluded.

| Rank (st. dif.) | | Toxicity | | | P value C.-A.** |
|---|---|---|---|---|---|
| | | Yes | No | (% of Yes) | |
| Rank_1 (2.16) | APCDD1L; rs1980576 (A > G): an alternative for rs3946003 as revealed by exome analysis | | | | |
| | A/A | 6 | 16 | (27.3) | 0.011 |
| | A/G | 20 | 20 | (50.0) | |
| | G/G | 8 | 3 | (72.7) | |
| Rank_2, 3 (1.98) | R3HCC1; rs2272761 (G > A): linked to rs13530 as revealed by exome analysis | | | | |
| | G/G | 0 | 6 | (0.0) | 0.050 |
| | G/A | 10 | 11 | (47.6) | |
| | A/A | 24 | 22 | (52.2) | |
| Rank_4 (1.81) | OR5I2; rs12577167 (A > G) | | | | |
| | A/A | 23 | 19 | (54.8) | 0.044 |
| | A/G | 10 | 14 | (41.7) | |
| | G/G | 1 | 6 | (14.3) | |
| Rank_5, 6 (1.73) | MKKS; rs1547 (C > T): linked to rs1545 as revealed by exome analysis | | | | |
| | C/C | 10 | 20 | (33.3) | 0.060 |
| | C/T | 19 | 16 | (54.3) | |
| | T/T | 5 | 3 | (62.5) | |
| Rank_7 (1.71) | CSMD2; rs474474 (A > G) | | | | |
| | A/A | 22 | 16 | (57.9) | 0.131 |
| | A/G | 8 | 18 | (30.8) | |
| | G/G | 4 | 5 | (44.4) | |
| Rank_8 (1.71) | EDEM3; rs9425343 (T > G) | | | | |
| | T/T | 13 | 8 | (61.9) | 0.080 |
| | T/G | 16 | 21 | (43.2) | |
| | G/G | 5 | 10 | (33.3) | |
| Rank_9 (1.71) | GATA2; rs2335052 (G > A) | | | | |
| | G/G | 17 | 14 | (54.8) | 0.452 |
| | G/A | 12 | 20 | (37.5) | |
| | A/A | 5 | 5 | (50.0) | |
| Rank_10 (1.50) | APCDD1L; rs7265854 (A > G) | | | | |
| | A/A | 18 | 13 | (58.1) | 0.019 |
| | A/G | 15 | 18 | (45.5) | |
| | G/G | 1 | 8 | (11.1) | |
| Rank_11 (1.38) | ACOX1; rs1135640 (C > G)***; N = 72 | | | | |
| | C/C | 8 | 3 | (72.7) | 0.004 |
| | C/G | 18 | 14 | (56.3) | |
| | G/G | 8 | 21 | (27.6) | |

**Cochran-Armitage trend test.
***Exome analysis (N = 15) revealed linkage to TRIM65 (rs3760128), TRIM65 (rs7222757), and FBF1 (rs2305913).

TABLE 5

N = 72 (subjects who were homozygous for UGT1A1*28 were excluded)

| | | Toxicity | | | Fisher's Exact Test | |
|---|---|---|---|---|---|---|
| | | Yes | No | (% of Yes) | P value | Odds ratio |
| Rank_1 | APCDD1L; rs1980576 (A > G): an alternative for rs3946003 as revealed by exome analysis | | | | | |
| | A/A | 6 | 16 | (27.3) | 0.039 | 0.300 |
| | A/G, G/G | 28 | 22 | (56.0) | | |
| | A/A, A/G | 26 | 35 | (42.6) | | |
| | G/G | 8 | 3 | (72.7) | 0.101 | 3.527 |
| Rank_2, 3 | R3HCC1; rs2272761 (G > A): linked to rs13530 as revealed by exome analysis | | | | | |
| | G/G | 0 | 6 | (0.0) | 0.026 | 0.000 |
| | G/A, A/A | 34 | 32 | (51.5) | | |
| Rank_8 | EDEM3; rs9425343 (T > G) | | | | | |
| | T/T | 13 | 7 | (65.0) | 0.071 | 2.702 |
| | T/G, G/G | 21 | 31 | (40.4) | | |
| Rank_10 | APCDD1L; rs7265854 (T > C) | | | | | |
| | T/T, T/C | 33 | 30 | (52.4) | | |
| | C/C | 1 | 8 | (11.1) | 0.030 | 0.116 |
| Rank_11 | ACOX1; rs1135640 (C > G)*** | | | | | |
| | C/C, C/G | 26 | 17 | (60.5) | | |
| | G/G | 8 | 21 | (27.6) | 0.008 | 0.254 |

***Exome analysis (N = 15) revealed linkage to TRIM65 (rs3760128), TRIM65 (rs7222757), and FBF1 (rs2305913).

As shown in Table 4, the occurrence of rs1980576, rs2272761, and rs1135640 as well as rs12577167 and rs7265854 tended to be significantly proportional to the incidence of a side effect of irinotecan in the 73 cases including cases where the subjects had been considered to have a high risk of a side effect in view of the UGT1A gene polymorphisms. Moreover, Table 5 revealed that the odds ratio, indicating the occurrence of hematologic toxicity, was 0.1 in the cases where the single nucleotide polymorphisms were homozygous for a variant type (C/C) with respect to rs7265854.

Accordingly, analyzed are: single nucleotide polymorphisms rs1980576 and rs7265854 in a region encoding the APCDD1L gene; a single nucleotide polymorphism rs2272761 in a region encoding the R3HCC1 gene; a single nucleotide polymorphism rs12577167 in a region encoding the OR5I2 gene; a single nucleotide polymorphism rs1547 in a region encoding the MKKS gene; a single nucleotide polymorphism rs9425343 in a region encoding the EDEM3 gene; and a single nucleotide polymorphism rs1135640 in a region encoding the ACOX1 gene. Then, by analyzing whether the single nucleotide polymorphism is homozygous for a variant type, homozygous for a wild-type, or heterozygous, it has been revealed that it is possible to accurately assist a prediction of a risk of occurrence of a side effect of irinotecan, which risk could not conventionally be predicted from the UGT1A gene polymorphisms.

Example 5

Patients (FOLFIRI; 72 cases) with colon cancer who had received irinotecan (3 cases were excluded from the 75 cases in Example 2) and patients (FOLFOX; 44 cases) with colon cancer who had not received irinotecan were analyzed with respect to rs2272761. The results are shown in Table 6.

TABLE 6

R3HCC1; rs2272761 (G > A)

| | Hematologic Toxicity | | |
|---|---|---|---|
| | Yes | No | (% of Yes) |
| FOLFIRI (n = 72) | | | |
| G/G | 0 | 6 | (0.0) |
| G/A | 10 | 10 | (50.0) |
| A/A | 24 | 22 | (52.2) |
| FOLFOX (n = 44) | | | |
| G/G | 0 | 3 | (0.0) |
| G/A | 5 | 16 | (23.8) |
| A/A | 2 | 18 | (10.0) |
| Total (N = 116) | | | |
| G/G | 0 | 9 | (0.0) |
| G/A | 15 | 26 | (36.6) |
| A/A | 26 | 40 | (39.4) |

The results of Table 6 revealed that not even a single case where the single nucleotide polymorphism was homozygous for a wild-type (G/G) with respect to rs2272761 exhibited hematologic toxicity regardless of the presence or absence of irinotecan.

INDUSTRIAL APPLICABILITY

The present invention can assist a prediction of a risk of occurrence of a side effect of irinotecan, and is thus applicable in the field of medicine.

The invention claimed is:

1. A method to prevent occurrence of one or more side effects of irinotecan during a cancer treatment, comprising:
   determining whether a patient with cancer has a genetic predisposition to having side effects when treated with irinotecan by:
      obtaining or having obtained a biological sample from the patient with cancer; and
      performing or having performed a genotyping assay on the biological sample by following steps (i) to (iv);
         (i) performing an amplifying reaction using, as a template, genomic DNA of a biological sample collected from the patient with cancer to amplify a nucleic acid fragment containing a single nucleotide polymorphism site present at nucleotide 2459 of a nucleotide sequence encoding an EDEM3 gene as set forth in SEQ ID NO: 5 using polymerase chain reaction using fluorescently-labeled primers;
         (ii) performing a hybridization between a resulting nucleic acid fragment and at least a first probe to a wild type allele and at least a second probe to a variant type allele;
            wherein the second probe comprises the single nucleotide polymorphism present at nucleotide 2459 of a nucleotide sequence encoding an EDEM3 gene as set forth in SEQ ID NO: 5 having a G at position 2459, a complementary nucleotide sequence thereof having a C at position 2459, or both; and
            wherein the first probe is to the wild type allele having T at position 2459, a complementary nucleotide sequence thereof having an A at position 2459, or both;
         (iii) measuring fluorescence intensities of the nucleic acid fragment hybridized with the first and the second probes; and
         (iv) calculating a ratio of the fluorescence intensities between the first and the second probes, and based on the ratio of the fluorescence intensities;
   determining if the patient is homozygous for the variant type allele, homozygous for the wild type allele, or heterozygous, and
   administering a cancer treatment other than irinotecan if the patient is homozygous for the wild type allele; or
   administering irinotecan to the patient if the patient with cancer is homozygous for the variant type allele or is heterozygous.

2. The method of claim 1, further comprising providing a kit for assisting the prediction of a risk of occurrence of the one or more side effects of irinotecan, comprising a probe that detects the variant type allele of the EDEM3 gene at position 2459 of SEQ ID NO: 5 and a probe that detects the wild type allele of the EDEM3 gene at position 2459 of SEQ ID NO: 5.

3. The method of claim 1, wherein the one or more side effects are leucopenia or neutropenia.

4. A method to prevent occurrence of one or more side effects of irinotecan when treating a patient with a cancer, comprising:
   determining whether the patient has a genetic predisposition to having side effects when treated with irinotecan by:
      obtaining or having obtained a biological sample from the patient with cancer; and
      performing or having performed a genotyping assay on the biological sample by following steps (i) to (iv);
         (i) performing an amplifying reaction using, as a template, genomic DNA of a biological sample collected from the patient with cancer to amplify a nucleic acid fragment containing a single nucleotide polymorphism site present at nucleotide 2459 of a nucleotide sequence encoding an EDEM3 gene as set forth in SEQ ID NO: 5 using polymerase chain reaction;
         (ii) performing a hybridization between a resulting nucleic acid fragment and at least a first probe to a wild type allele and at least a second probe to a variant type allele;
            wherein the first probe is to the wild type allele having T at position 2459, a complementary nucleotide sequence thereof having an A at position 2459, or both; and
            wherein the second probe comprises the single nucleotide polymorphism present at nucleotide 2459 of a nucleotide sequence encoding an EDEM3 gene as set forth in SEQ ID NO: 5 having a G at position 2459, a complementary nucleotide sequence thereof having a C at position 2459, or both;
(iii) comparing an amount of nucleic acid fragment hybridized with the first and the second probes; and
(iv) calculating a ratio between the first and the second probes; and determining if the patient is homozygous for the variant type allele, homozygous for the wild type allele, or heterozygous, and if the patient is homozygous for the wild type allele administering a cancer treatment other than irinotecan; or if the patient with cancer is homozygous or heterozygous for the variant type allele, administering irinotecan to the patient.

5. The method of claim 4, further comprising providing a kit for assisting the prediction of a risk of occurrence of the one or more side effects of irinotecan, comprising a probe that detects the variant type allele of the EDEM3 gene at position 2459 of SEQ ID NO: 5 and a probe that detects the wild type allele of the EDEM3 gene at position 2459 of SEQ ID NO: 5.

6. The method of claim 4, wherein the one or more side effects are leucopenia or neutropenia.

7. The method of claim 4, wherein the amount of nucleic acid fragment hybridized with the first and the second probes is determined by fluorescence.

8. A method of treating a patient with a cancer, comprising:
determining whether the patient has a genetic predisposition to having side effects when treated with irinotecan by:
obtaining or having obtained a biological sample from the patient with cancer; and
performing or having performed a genotyping assay on the biological sample by following steps (i) to (iv);
(i) performing an amplifying reaction using, as a template, genomic DNA of the biological sample to amplify a nucleic acid fragment containing a single nucleotide polymorphism site present at nucleotide 2459 of a nucleotide sequence encoding an EDEM3 gene as set forth in SEQ ID NO: 5 using polymerase chain reaction;
(ii) performing a hybridization between a resulting nucleic acid fragment and at least a first probe to a wild type allele and at least a second probe to a variant type allele;
wherein the first probe is to the wild type allele having T at position 2459, a complementary nucleotide sequence thereof having an A at position 2459, or both; and
wherein the second probe comprises the single nucleotide polymorphism present at nucleotide 2459 of a nucleotide sequence encoding an EDEM3 gene as set forth in SEQ ID NO: 5 having a G at position 2459, a complementary nucleotide sequence thereof having a C at position 2459, or both;
(iii) comparing an amount of nucleic acid fragment hybridized with the first and the second probes; and
(iv) calculating a ratio between the first and the second probes;

determining if the patient is homozygous for the variant type allele, homozygous for the wild type allele, or heterozygous, and administering a cancer treatment other than irinotecan if the patient is homozygous for the wild type allele; or administering irinotecan to the patient if the patient with cancer is homozygous for the variant type allele or heterozygous.

\* \* \* \* \*

SEQUENCE LISTING

```
<160> NUMBER OF SEQ ID NOS: 13

<210> SEQ ID NO 1
<211> LENGTH: 1506
<212> TYPE: DNA
<213> ORGANISM: Homo sapiens
<220> FEATURE:
<223> OTHER INFORMATION: Inventor: Oka, Masaaki
     Inventor: Hazama, Shoichi
     Inventor: Tsunedomi, Ryouichi

<400> SEQUENCE: 1
atgcccgcag ccatgctccc ctacgcttgc gtcctggtgc ttttgggagc ccacactgca      60
ccggcggctg gggaggccgg gggcagctgc ctgcgctggg aaccccactg ccagcagccc     120
ttgccagata gagtgcccag cactgcgatc ctgcctccac gccttaatgg accttggatc     180
tccacaggct gcgaggtgcg cccaggaccg gagttcctga cccgcgccta caccttctac     240
cccagccggc tctttcgagc ccaccagttc tactacgagg acccccttctg cggggaacct    300 gcccactcgc tgctcgtcaa gggcaaagtc cgcctgcgcc gggcctcctg ggtcacccgg    360
ggagccaccg aggccgacta ccacctgcac aaggtgggca tcgtcttcca cagccgccgg    420
gccctggtcg acgtcaccgg gcgcctcaac cagacccgcg ccggccggga ctgcgcgcgg    480
cggctgcctc cggcccgggc ctggctgcct ggggcgctgt acgagctgcg gagcgcccgg    540
gctcaggggg actgcctgga ggcgctgggc ctcaccatgc acgagctcag cctggtccgc    600
gtgcagcgcc gcctgcagcc gcagccccgg gcgtcgcccc ggctggtgga ggagctgtac    660
ctgggggaca tccacaccga cccggcggag aggcggcact accggcccac gggctaccag    720
cgcccgctgc agagcgcact gcaccacgtg cagccgtgcc cagcctgtgg cctcattgcc    780
cgctccgatg tgcaccaccc gcccgtgctg ccgccccctc tggccctgcc cctgcacctg    840
ggcggctggt gggtcagctc ggggtgcgag gtgcgccagc cagtcctgtt cctcacccgg    900
ctcttcactt tccacgggca cagccgctcc tgggaagggt attaccacca cttctcagac    960
ccagcctgcc ggcagcccac cttcaccgtg tatgccgccg gccgctacac caggggcacg   1020
ccatccacca gggtccgcgg cggcaccgag ctggtgtttg aggtcacacg ggcccatgtg   1080
```

```
acccccatgg accaggtcac cacggccatg ctcaacttct ctgagccaag cagctgtggg      1140
ggtgcggggg cctggtccat ggcactgagc cgggatgtca cagccaccaa cggctgccta      1200
ccgctgggca tccggctccc gcatgtggag tacgagcttt tcaagatgga acaagacccc      1260
ctcgggcaaa gcctgctctt catcggacaa aggcccaccg atggctcaag tcccgatacc      1320
ccagagaaac gtcccacctc ctaccaagca cccctggtgc tctgtcatgg ggaggccccc      1380
gacttctcca ggccaccgca gcacaggcca tcgctgcaga agcacccag cacagggggt       1440 cttcacatag cccccttccc acttctgccc ctagttctag ggctggcctt cctccactgg      1500
ctatga                                                                 1506

<210> SEQ ID NO 2
<211> LENGTH: 762
<212> TYPE: DNA
<213> ORGANISM: Homo sapiens

<400> SEQUENCE: 2
atgactcagg gaacagagga cctaaagggc ccaggacaaa ggtgtgagaa tgagccactg       60
ctggaccctg ttggccctga gcctctgggg cctgagagtc agtcaggaa gggagacatg      120 gtggagatgc ccacacggtt tgggtccacc ctgcagctag acctgaaaaa ggggaaggag      180
agtctgttgg agaagaggct ggtggcagag gaggaagagg acgaagagga ggtggaagag      240
gatggcccca gcagctgctc ggaggacgat tacagtgagc tgctgcagga gatcacagac      300
aacctgacga agaaggagat tcagatagag aagatccatt tggacacatc ctccttcgtg      360
gaggagctgc ctggagagaa ggaccttgcc cacgtggtag agtctatga ctttgaacca      420 gcgctcaaga cggaggacct gctggcaacg ttttctgagt tccaagagaa ggggttcagg      480
attcagtggg tggatgatac tcacgcactc ggcatctttc cctgcctggc ctcagctgcg      540
gaagccctga cccgggagtt ctcggtgctc aagatccggc ccctcacaca gggaaccaag      600
cagtcaaagc tcaaagcctt gcagaggcca aaactcctgc gtctggtgaa ggagaggcca      660
cagacaaatg cgactgtggc ccggcggctg gtggcccggg ccctgggact ccaacacaaa      720
aagaaagagc ggcctgctgt ccggggtccg ctgccgccct ga                         762

<210> SEQ ID NO 3
<211> LENGTH: 939
<212> TYPE: DNA
<213> ORGANISM: Homo sapiens

<400> SEQUENCE: 3
atggggttgt tcaatgtcac tcaccctgca ttcttcctcc tgactggtat ccctggtctg       60
gagagctctc actcctggct gtcagggccc ctctgcgtga tgtatgctgt ggcccttggg      120
ggaaatacag tgatcctgca ggctgtgcga gtggagccca gcctccatga gcccatgtac      180
tacttcctgt ccatgttgtc cttcagtgat gtggccatat ccatggccac actgcccact      240
gtactccgaa cctctgcct caatgcccgc aacatcactt tgatgcctg tctaattcag      300 atgtttctta ttcacttctt ctccatgatg aatcaggta ttctgctggc catgagtttt      360
gaccgctatg tggccatttg taccccttg cgctatgcaa ctgtgctcac cactgaagtc      420
attgctgcaa tgggtttagg tgcagctgct cgaagcttca tcacccttt ccctcttccc      480 tttcttatta gaggctgcc tatctgcaga tccaatgttc tttctcactc ctactgcctg      540
cacccagaca tgatgaggct tgcctgtgct gatatcagta tcaacagcat ctatggactc      600
tttgttcttg tatccacctt tggcatggac ctgttttta tcttcctctc ctatgtgctc      660
```

| | |
|---|---|
| attctgcgtt ctgtcatggc cactgcttcc cgtgaggaac gcctcaaagc tctcaacaca | 720 |
| tgtgtgtcac atatcctggc tgtacttgca ttttatgtgc caatgattgg ggtctccaca | 780 |
| gtgcaccgct ttgggaagca tgtcccatgc tacatacatg tcctcatgtc aaatgtgtac | 840 |
| ctatttgtgc ctcctgtgct caaccctctc atttatagcg ccaagacaaa ggaaatccgc | 900 |
| cgagccattt tccgcatgtt tcaccacatc aaaatatga | 939 |

<210> SEQ ID NO 4
<211> LENGTH: 1713
<212> TYPE: DNA
<213> ORGANISM: Homo sapiens

<400> SEQUENCE: 4

| | |
|---|---|
| atgtctcgtt tggaagctaa gaagccatca ttgtgtaaga gtgaaccact gacaactgag | 60 |
| agagtcagga ccacactttc tgtcttgaaa agaattgtaa catcatgcta tggcccctca | 120 |
| ggtaggctga agcagctgca caatggcttt ggaggttacg tgtgtacaac ctcacagtcc | 180 |
| tcagctctgc tcagtcacct tttggtcaca catcccattt aaagatcct gacagcctcc | 240 |
| atacagaatc atgtgtcaag cttcagtgat tgtggcttat tcacagctat tctttgctgc | 300 |
| aacctgattg aaaatgttca gagattaggc ttgacaccca ccactgtcat tagattaaat | 360 |
| aaacatcttt tgagtctttg catcagttat ctcaagtctg agacctgtgg ttgtcgaatc | 420 |
| ccagtggact ttagtagtac tcagatcctc ctttgtttgg tgcgtagtat attaacaagt | 480 |
| aaacctgcct gtatgctcac cagaaaggaa acagagcatg tcagtgcttt gatcctgaga | 540 |
| gccttttgc ttacaattcc agaaaatgct gaaggccaca tcatttagg aaagagttta | 600 |
| attgtacctt taaaaggtca aagagttata gattccactg tattacctgg gatactcatt | 660 |
| gaaatgtcag aagttcaatt aatgaggcta ttacctatca aaaaatcaac tgccctcaag | 720 |
| gtggcactct tttgtacaac tttatccgga gacacttctg acactggaga aggaactgtg | 780 |
| gtggtcagtt atggggtttc tcttgaaaat gcagtcttgg accagctgct taacctagga | 840 |
| aggcagctaa tcagtgacca cgtagatctt gtcctgtgcc aaaaagttat acatccatct | 900 |
| ttgaagcagt ttctcaatat gcatcgtatt attgccatag acagaattgg agtgactctg | 960 |
| atggaacccc tgactaaaat gacaggaaca cagcctattg gatccctagg ctcaatatgt | 1020 |
| cctaatagtt atggaagtgt gaaagatgtg tgcactgcaa atttggctc caaacatttt | 1080 |
| tttcatctta ttcctaatga agcaacaatc tgcagcttgc ttctctgcaa cagaaatgac | 1140 |
| actgcctggg atgagctgaa gctcacgtgt cagacggcac tgcatgtcct gcagttaaca | 1200 |
| ctcaaggaac catgggcttt gttgggaggt ggctgtactg aaactcattt ggctgcatat | 1260 |
| atcagacaca agactcacaa cgacccagaa agcattctca agatgatga atgtactcaa | 1320 |
| acagaacttc aattaattgc tgaagcattt tgcagtgccc tagaatctgt tgttggctct | 1380 |
| ttagaacatg atggaggtga aattctcact gacatgaagt atggacacct ttggtcagtt | 1440 |
| caggcagatt ctccctgtgt tgctaactgg ccagatttgc tttcacagtg tggctgtgga | 1500 |
| ttatacaata gccaggaaga actcaactgg tctttcttaa gaagcacacg tcgtccattt | 1560 |
| gtgccacaaa gctgccttcc acatgaagct gtgggctcag ccagcaacct gaccttggac | 1620 |
| tgtttgactg caaagcttag tggcctacag gtggctgtag agacagccaa tttgattttg | 1680 |
| gatctttcat atgttattga agataaaaac taa | 1713 |

<210> SEQ ID NO 5

-continued

```
<211> LENGTH: 2799
<212> TYPE: DNA
<213> ORGANISM: Homo sapiens

<400> SEQUENCE: 5
atgagcgaag ccggcggccg gggctgtggg tccccggttc cccagcgagc gcgatggaga      60
ctagtggcgg cgacggccgc gttctgcctg gtgtcggcca cctccgtgtg gacggcgggg     120
gccgagccca tgagtaggga ggagaaacag aagcttggga atcaagtact ggaaatgttt     180
gatcatgctt atggtaacta tggaacat gcttaccctg ctgatgaact catgccttta      240
acctgtagag gtcgagttag aggccaagag ccaagtcgcg gtgacgttga tgatgccttg     300
ggaaaatttt ctctgacact gattgattct ttggacactc ttgtggtttt aaataaaact     360
aaagaatttg aagatgcagt gagaaaagtt taagagatg ttaatttaga taacgatgta      420
gtcgtatcag tctttgaaac aaacatcaga gttcttgggg tcttttggg tgggcactcc     480 ctggcaatca tgctgaaaga aaaggtgaa tatatgcagt ggtacaatga tgaacttctc      540
caaatggcaa agcagttagg ttacaaactt ttaccggctt tcaacactac cagtggcctt     600
ccttatccaa gaattaattt aaagtttggc atcagaaaac cagaagctcg gacaggaact     660
gagacagata cctgtacagc ttgtgcaggt accttgatcc ttgaatttgc tgctttaagt     720
cgattcacag gagcaacaat atttgaggaa tatgccagaa aagctcttga ttttctctgg     780
gaaaaaagac agcgaagtag taatttagtg ggcgtgacta taaatattca tactggagat     840
tgggtacgaa agatagtgg agttggagca gggattgatt catattatga atatctgttg     900
aaagcctatg tcttgcttgg agatgacagt tttctggaaa gatttaacac acactatgat     960
gccataatga ggtatattag ccagccacct cttctacttg atgtgcatat ccacaaacca    1020
atgctgaatc tcggacttg gatggatgct ttgcttgcct tcttcccagg cttgcaggtg     1080
ttaaaggggg atattagacc tgctattgaa actcatgaaa tgttatatca ggtgattaaa    1140
aaacacaatt ttctaccaga ggcatttacc acagatttca gagtacactg gctcaacat      1200 cctttaaggc agaatttgc agaaagtacc tacttcttat ataaagctac aggagatcct     1260
tactaccttg aagtagggaa gacacttatt gaaaatttaa ataaatatgc tagagtgcct     1320
tgcggatttg ctgccatgaa ggatgttcgt actggaagtc atgaggacag aatggattct    1380
ttcttcttgg ctgaaatgtt taaatatctt tacctgttat ttgctgataa agaagacatt    1440 attttttgaca tagaagatta catctttaca acagaagctc atctgttacc tctttggctc    1500
tctactacaa atcaaagcat ctctaaaaag aacacaaccct cggaatatac agaactggat    1560
gacagtaact tcgattggac ttgtccaaat actcagatcc tctttcctaa tgacccattg    1620
tatgctcaaa gtattcgtga gcccttgaaa aatgtggtgg ataagagctg tcctagaggc    1680
atcatcagag tagaggagag tttcaggagt ggagctaaac cccctctgag agccagagat    1740
ttcatggcca ctaaccctga gcatttagaa atcctgaaga gatgggggt gagtttgatt    1800 cacctcaaag atgggagagt ccagttggtc caacatgcaa tccaagctgc tagttcaatc    1860
gacgctgaag atgggttgag gttcatgcag gagatgattg aattgtcaag tcagcaacaa    1920
aaagaacagc agctgcctcc acgagctgta caaattgttt cccacccatt ttttggcagg    1980
gtagtattga ctgctggacc agctcagttt gggctggatc tgtctaaaca taagagaca     2040 agaggatttg ttgcaagcag taaaccatcc aatggttgtt cagagcttac taacccagag    2100
gcagtgatgg gaaaaatcgc actgataaca agaggacagt gcatgtttgc agaaaaggca    2160
cgcaacatcc agaatgctgg agccattggt ggcattgtta ttgatgacaa tgaggggagc    2220
```

| | |
|---|---|
| agcagtgata ctgcccctct gttccagatg gcaggtgatg gaaaggatac agatgacatc | 2280 |
| aagatcccca tgctgttctt attcagcaaa gaaggaagta tcatactgga tgccatccgg | 2340 |
| gaatatgagg aggtagaagt gctcctctct gataaagcaa agatcgaga tcctgaaatg | 2400 |
| gaaaatgaag aacaaccatc ctctgaaaat gattctcaga atcagagtgg tgaacagatt | 2460 |
| tcatcaagtt ctcaggaggt tgatttggtt gatcaagagt cttctgagga aaattctcta | 2520 |
| aattctcacc cagaatcatt atctctagca gatatgggaca atgctgcaag catttcccct | 2580 |
| tctgaacaga cttctaatcc cacagaaaac catgagacta caaatcttaa tggtgaatgt | 2640 |
| acagatttag ataaccagct tcaagaacaa tcagaaactg aggaagattc caatcctaat | 2700 |
| gttagctggg gtaaaaaggt ccagcctata gactccatat tagcagactg gaatgaagat | 2760 |
| atagaagcat ttgaaatgat ggagaaggat gagctatga | 2799 |

<210> SEQ ID NO 6
<211> LENGTH: 1983
<212> TYPE: DNA
<213> ORGANISM: Homo sapiens

<400> SEQUENCE: 6

| | |
|---|---|
| atgaacccgg acctgcgcag ggagcgggat ccgccagct tcaacccgga gctgcttaca | 60 |
| cacatcctgg acggcagccc cgagaaaacc cggcgccgcc gagagatcga gaacatgatc | 120 |
| ctgaacgacc cagacttcca gcatgaggac ttgaacttcc tcactcgcag ccagcgttat | 180 |
| gaggtggctg tcaggaaaag tgccatcatg gtgaagaaga tgagggagtt tggcatcgct | 240 |
| gaccctgatg aaattatgtg gtttaaaaat tttgtgcacc gagggcggcc tgagcctctg | 300 |
| gatcttcact tgggcatgtt cctgcccacc ttgcttcacc aggcaactgc ggagcagcag | 360 |
| gagcgcttct tcatgcccgc ctggaacttg agatcattg gcacttatgc ccagacagag | 420 |
| atgggtcatg gaactcacct tcgaggcttg gaaaccacag ccacgtatga ccctgaaacc | 480 |
| caggagttca ttctcaacag tcctactgtg acctccatta atggtggcc tggtgggctt | 540 |
| ggaaagactt caaatcatgc aatagttctt gcccagctca tcactaaggg gaaatgctat | 600 |
| ggattacatg cctttatcgt acctattcgt gaaatcggga cccataagcc tttgccagga | 660 |
| attaccgttg gtgacatcgg ccccaaattt ggttatgatg agatagacaa tggctacctc | 720 |
| aaaatggaca ccatcgtat tcccagagaa acatgctga tgaagtatgc ccaggtgaag | 780 |
| cctgatggca catacgtgaa accgctgagt aacaagctga cttacgggac catggtgttt | 840 |
| gtcaggtcct tccttgtggg agaagctgct cgggctctgt ctaaggcgtg caccattgcc | 900 |
| atccgataca gcgctgtgag gcaccagtct gaaatcaagc caggtgaacc agaaccacag | 960 |
| attttggatt tcaaacccca gcagtataaa ctctttccac tcctggccac tgcctatgcc | 1020 |
| ttccagtttg tgggcgcata catgaaggag acctatcacc ggattaacga aggcattggt | 1080 |
| caagggacct gagtgaact gcctgagctt catgccctca ccgctggact gaaggctttc | 1140 |
| acctcctgga ctgcaaacac tggcattgaa gcatgtcgga tggcttgtgg tgggcatggc | 1200 |
| tattctcatt gcagtggtct tccaaatatt tatgtcaatt tcaccccaag ctgtaccttt | 1260 |
| gagggagaaa acactgtcat gatgctccag acggctaggt tcctgatgaa aagttatgat | 1320 |
| caggtgcact caggaaagtt ggtgtgtggc atggtgtcct atttgaacga cctgcccagt | 1380 |
| cagcgcatcc agccacagca ggtagcagtc tggccaacca tggtggatat caacagcccc | 1440 |
| gaaagcctaa ccgaagcata taactccgt gcagccagat tagtagaaat tgctgcaaaa | 1500 |

-continued

| | |
|---|---|
| aaccttcaaa aagaagtgat tcacagaaaa agcaaggagg tagcttggaa cctaacttct | 1560 |
| gttgaccttg ttcgagcaag tgaggcacat tgccactatg tggtagttaa gctcttttca | 1620 |
| gaaaaactcc tcaaaattca agataaagcc attcaagctg tcttaaggag tttatgtctg | 1680 |
| ctgtattctc tgtatggaat cagtcagaac gcgggggatt tccttcaggg gagcatcatg | 1740 |
| acagagcctc agattacaca agtaaaccag cgtgtaaagg agttactcac tctgattcgc | 1800 |
| tcagatgctg ttgctttggt tgatgcattt gattttcagg atgtgacact tggctctgtg | 1860 |
| cttggccgct atgatgggaa tgtgtatgaa aacttgtttg agtgggctaa gaactcccca | 1920 |
| ctgaacaaag cagaggtcca cgaatcttac aagcacctga agtcactgca gtccaagctc | 1980 |
| tga | 1983 |

```
<210> SEQ ID NO 7
<211> LENGTH: 51
<212> TYPE: DNA
<213> ORGANISM: artificial
<220> FEATURE:
<223> OTHER INFORMATION: rs1980576

<400> SEQUENCE: 7
```

| | |
|---|---|
| gtcaggatga cctgaagtct tacccygtgg agatccaagg tccattaagg c | 51 |

```
<210> SEQ ID NO 8
<211> LENGTH: 51
<212> TYPE: DNA
<213> ORGANISM: artificial
<220> FEATURE:
<223> OTHER INFORMATION: rs7265854

<400> SEQUENCE: 8
```

| | |
|---|---|
| tgggctcgaa agagccggct ggggtrgaag gtgtaggcgc gggtcaggaa c | 51 |

```
<210> SEQ ID NO 9
<211> LENGTH: 51
<212> TYPE: DNA
<213> ORGANISM: artificial
<220> FEATURE:
<223> OTHER INFORMATION: rs2272761

<400> SEQUENCE: 9
```

| | |
|---|---|
| tccttctctc caggcagctc ctccaygaag gaggatgtgt ccaaatggat c | 51 |

```
<210> SEQ ID NO 10
<211> LENGTH: 51
<212> TYPE: DNA
<213> ORGANISM: artificial
<220> FEATURE:
<223> OTHER INFORMATION: rs12577167

<400> SEQUENCE: 10
```

| | |
|---|---|
| catttgtgac cccttgcgct atgcarctgt gctcaccact gaagtcattg c | 51 |

```
<210> SEQ ID NO 11
<211> LENGTH: 51
<212> TYPE: DNA
<213> ORGANISM: artificial
<220> FEATURE:
<223> OTHER INFORMATION: rs1547

<400> SEQUENCE: 11
```

| | |
|---|---|
| cagctttgtg gcacaaatgg acgacrtgtg cttcttaaga aagaccagtt g | 51 |

```
<210> SEQ ID NO 12
<211> LENGTH: 51
<212> TYPE: DNA
<213> ORGANISM: artificial
<220> FEATURE:
<223> OTHER INFORMATION: rs9425343

<400> SEQUENCE: 12
atcaacctcc tgagaacttg atgaamtctg ttcaccactc tgattctgag a         51

<210> SEQ ID NO 13
<211> LENGTH: 51
<212> TYPE: DNA
<213> ORGANISM: artificial
<220> FEATURE:
<223> OTHER INFORMATION: rs1135640

<400> SEQUENCE: 13
gcgctgtgag gcaccagtct gaaatsaagc cagggtaagg atagggtcct a         51
```